(12) United States Patent
Geromanos et al.

(10) Patent No.: US 10,495,647 B2
(45) Date of Patent: Dec. 3, 2019

(54) ANALYSIS OF COMPLEX BIOLOGICAL MATRICES THROUGH TARGETING AND ADVANCED PRECURSOR AND PRODUCT ION ALIGNMENT

(71) Applicant: Waters Technologies Corporation, Milford, MA (US)

(72) Inventors: Scott J Geromanos, Middletown, NJ (US); Steven J Ciavarini, Natick, MA (US); James I. Langridge, Sales (GB); Brad J Williams, Salem, MA (US); Michael J Nold, Haverhill, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 15/318,239

(22) PCT Filed: Jun. 12, 2015

(86) PCT No.: PCT/US2015/035555
§ 371 (c)(1),
(2) Date: Dec. 12, 2016

(87) PCT Pub. No.: WO2015/191999
PCT Pub. Date: Dec. 17, 2015

(65) Prior Publication Data
US 2017/0108508 A1   Apr. 20, 2017

Related U.S. Application Data

(60) Provisional application No. 62/011,655, filed on Jun. 13, 2014.

(51) Int. Cl.
*G01N 33/68* (2006.01)
*H01J 49/00* (2006.01)
(Continued)

(52) U.S. Cl.
CPC ...... *G01N 33/6848* (2013.01); *H01J 49/0031* (2013.01); *H01J 49/421* (2013.01); *G01N 30/72* (2013.01)

(58) Field of Classification Search
None
See application file for complete search history.

(56) References Cited

U.S. PATENT DOCUMENTS

| | | | |
|---|---|---|---|
| 2003/0155505 A1* | 8/2003 | Russ, IV | H01J 49/0009 250/288 |
| 2012/0109533 A1 | 5/2012 | Kwon et al. | |

(Continued)

FOREIGN PATENT DOCUMENTS

WO    2012/099971 A2    7/2012

OTHER PUBLICATIONS

Egertson, J. et al., "*Multiplexed MS/MS for Improved Data Independent Acquisition*", Nat. Methods, (Aug. 2013).
(Continued)

*Primary Examiner* — Xiaoyun R Xu

(57) ABSTRACT

A method of mass spectrometry comprises ionising a sample eluting from a separation device in order to generate a plurality of parent ions. Multiple cycles of operation are performed as the sample elutes from the separation device. Each cycle of operation comprises mass analysing the parent ions to obtain parent ion mass spectral data, and mass analysing fragment or product ions derived from the parent ion to obtain fragment or product ion mass spectral data. Each cycle of operation also comprises mass analysing fragment or product ions derived from parent ions having mass to charge ratios within a first range to obtain first fragment or product ion mass spectral data, and mass analysing fragment or product ions derived from parent ions having mass to charge ratios within a second different range to obtain second fragment or product ion mass spectral data. The method can provide a hybrid data independent acquisition (DIA) and data dependent acquisition (DDA) approach.

19 Claims, 16 Drawing Sheets

(51) Int. Cl.
  *H01J 49/42*   (2006.01)
  *G01N 30/72*   (2006.01)

(56)          References Cited

U.S. PATENT DOCUMENTS

2012/0259557 A1    10/2012  Gorenstein et al.
2013/0299688 A1    11/2013  Balough et al.
2014/0034826 A1     2/2014  Geromanos et al.
2015/0041636 A1*    2/2015  Giles .................... H01J 49/004
                                                     250/282

OTHER PUBLICATIONS

Extended European Search Report for EP Patent Application No. 15806730.6 dated Jan. 24, 2018.
Bateman, R. H., et al., "A novel precursor ion discovery method on a hybrid quadrupole orthogonal acceleration time-of-flight (Q-TOF) mass spectrometer for studying protein phosphorylation", Journal of the American Society for Mass Spectrome, Elsevier Science Inc, vol. 13, No. 7, pp. 792-803, Jul. 1, 2002.

* cited by examiner

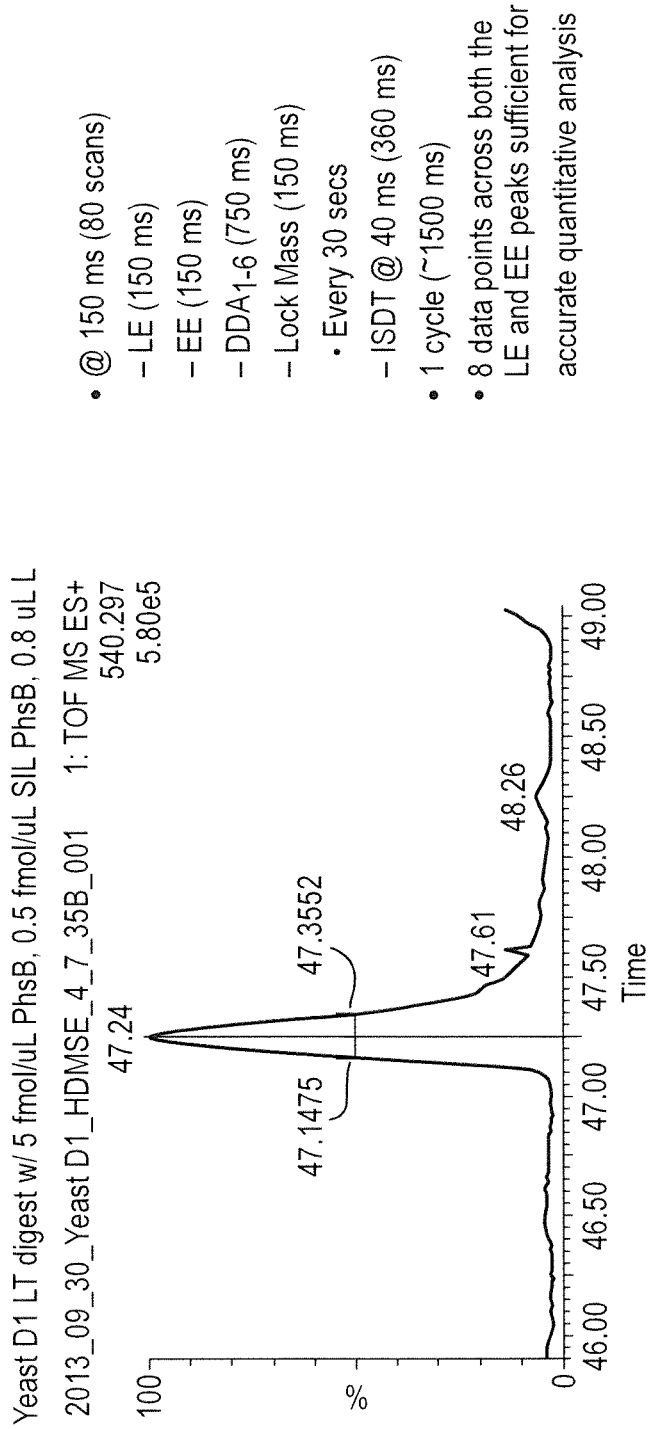

Fig. 4B
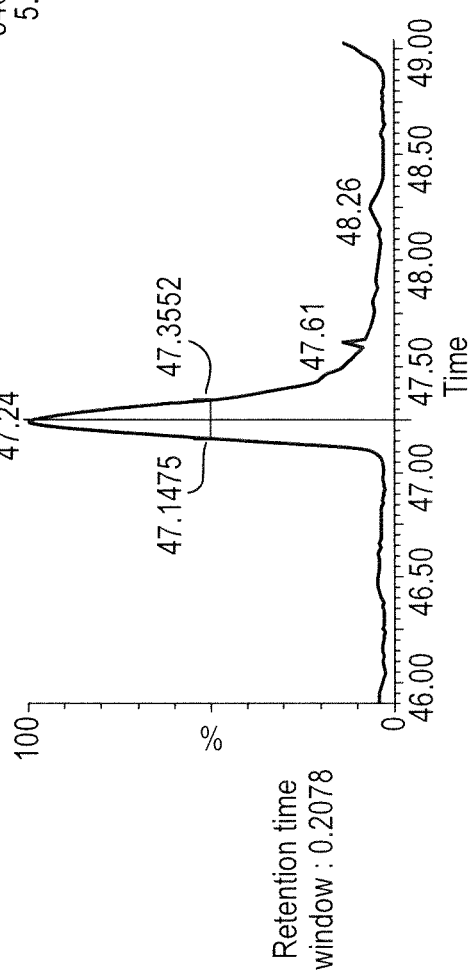
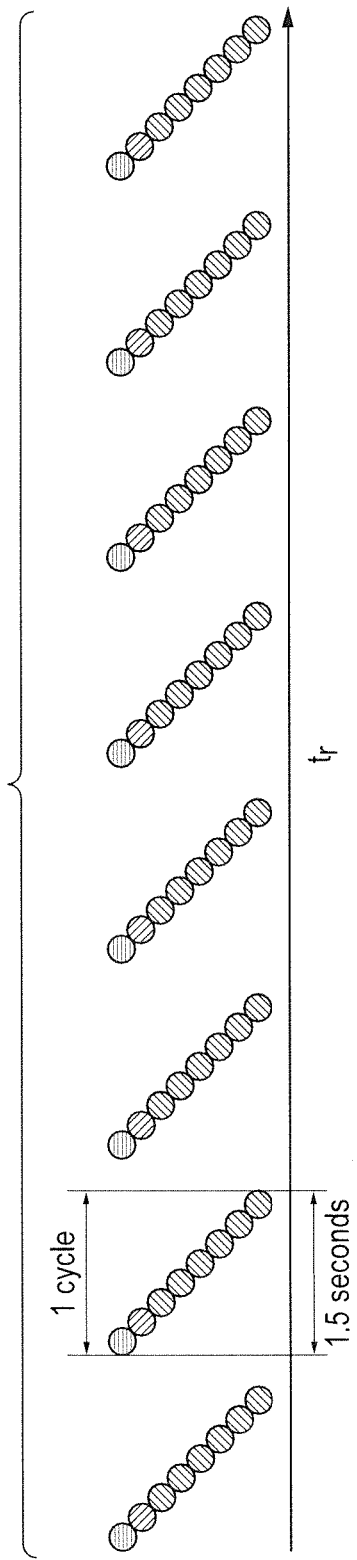

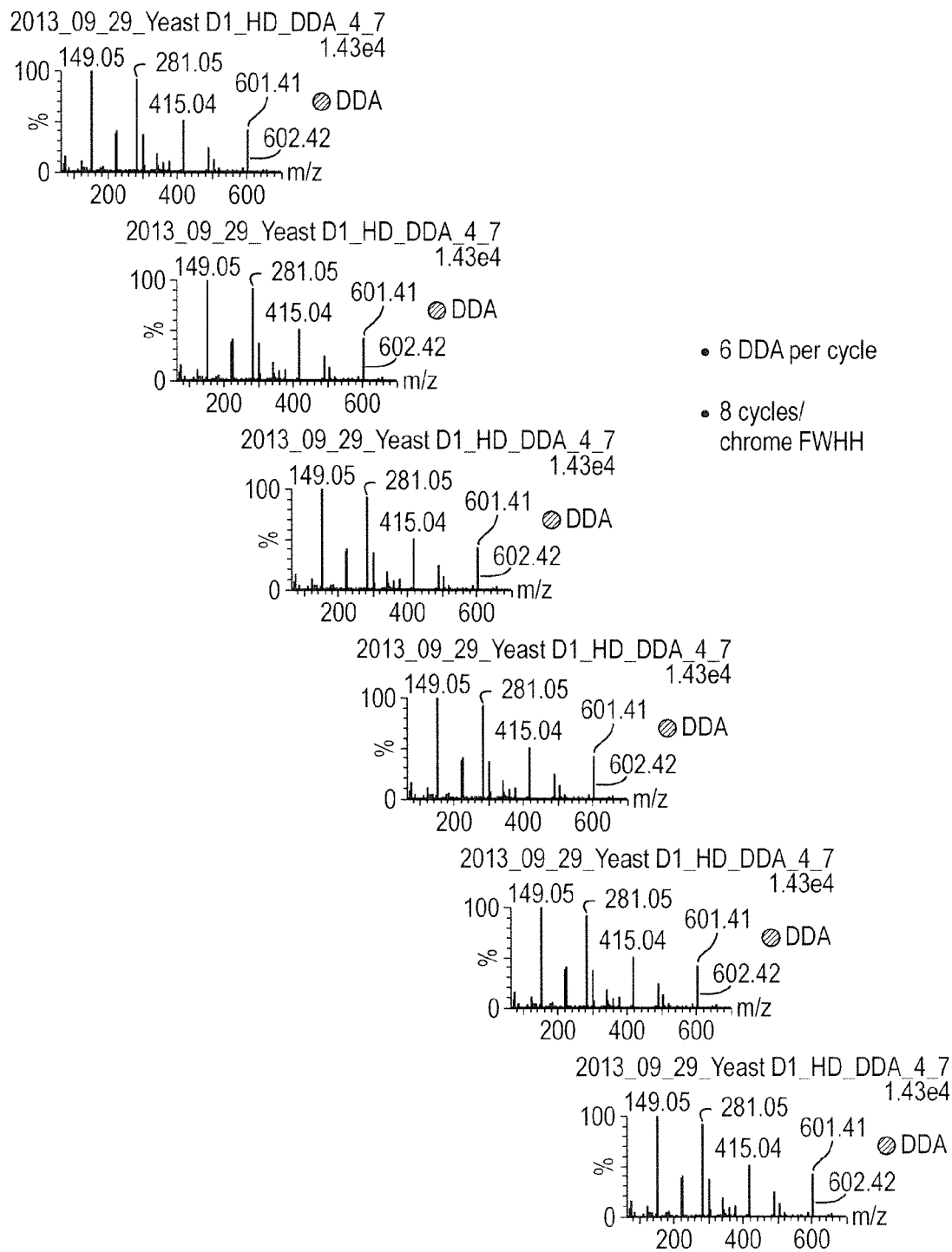

Fig. 6A
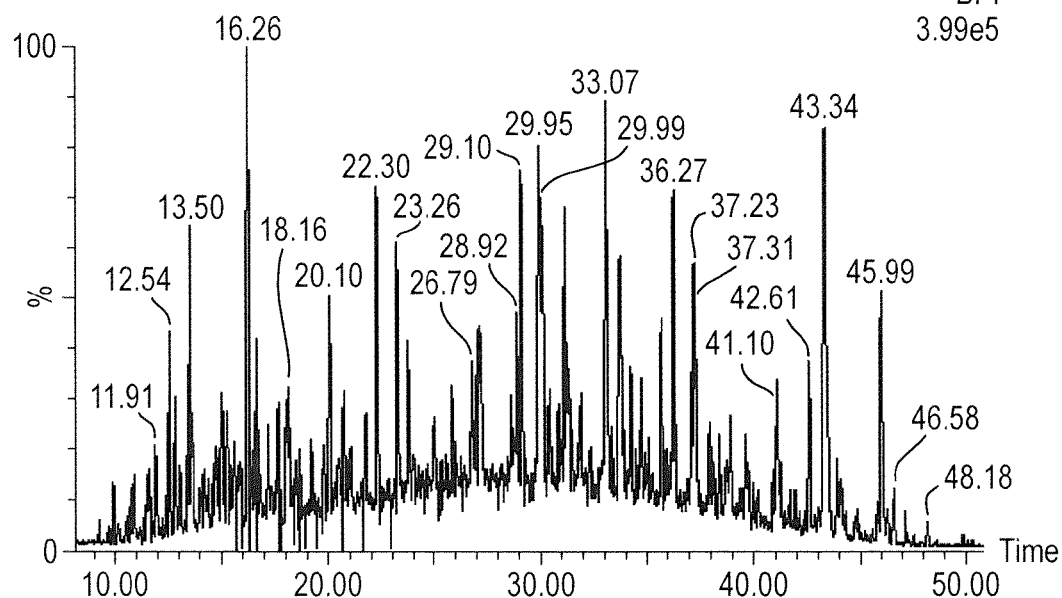
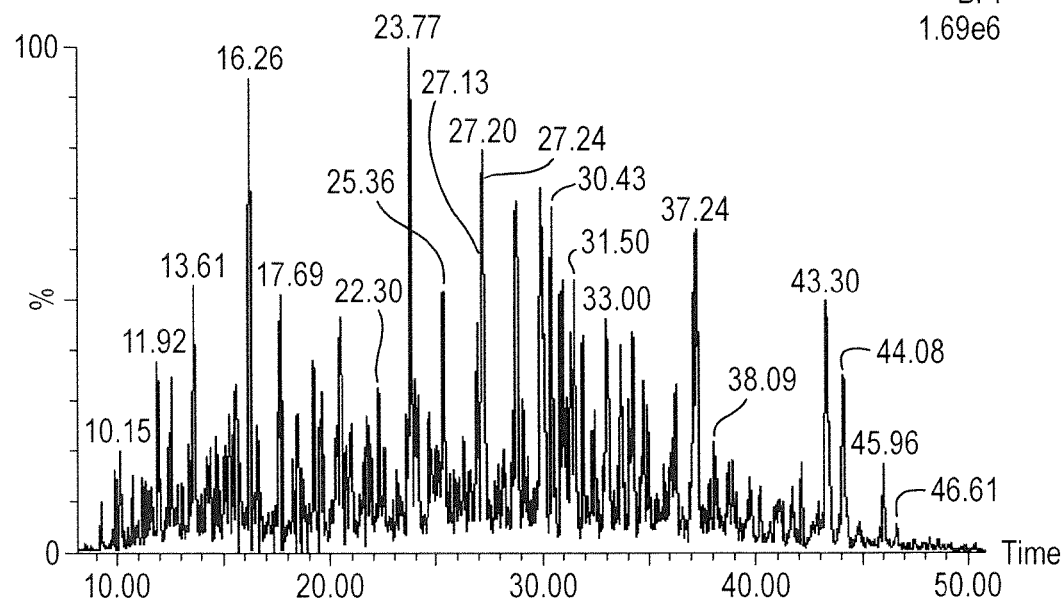

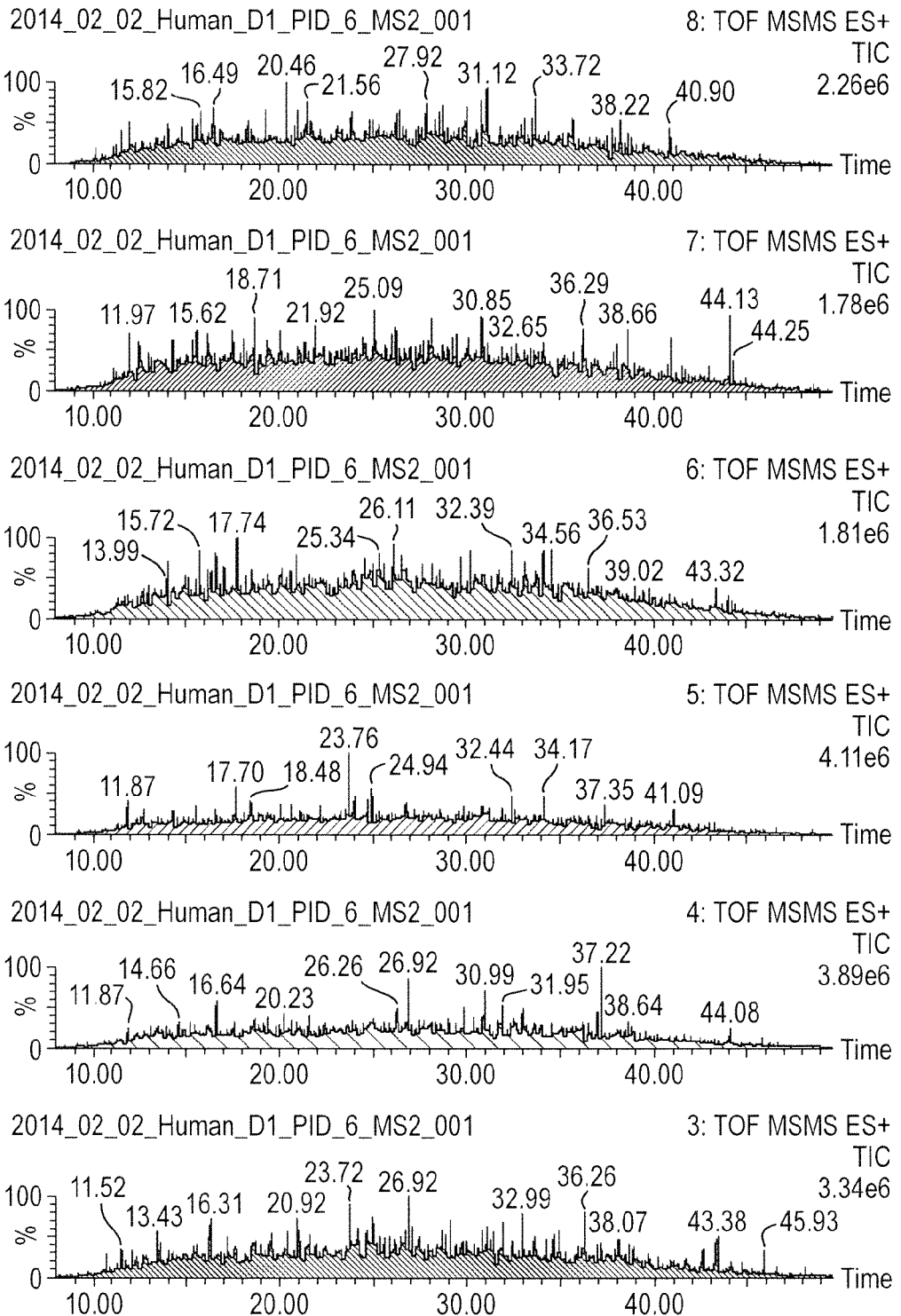

ANALYSIS OF COMPLEX BIOLOGICAL MATRICES THROUGH TARGETING AND ADVANCED PRECURSOR AND PRODUCT ION ALIGNMENT

CROSS-REFERENCE TO RELATED APPLICATIONS

This application represents the U.S. national Phase of International Application No. PCT/US2015/035555 entitled "Analysis of Complex Biological Matrices Through Targeting and Advance Precursor and Product Ion Alignment" filed 12 Jun. 2016, which claims priority from and benefit of U.S. provisional patent application Ser. No. 62/011,655 filed on 13 Jun. 2014. The entire contents of these applications are incorporated herein by reference.

FIELD OF THE INVENTION

The present invention relates generally to a method of mass spectrometry and a mass spectrometer.

BACKGROUND

The ability to acquire both accurate and precise qualitative and quantitative mass spectral data in the analysis of complex systems such as proteins is predicated on the ability to measure the physico-chemical attributes of all ions independent of any surrounding matrix.

Successful qualitative analysis requires ensuring that fragment and product ions are correctly aligned or matched to the parent or precursor ions from which they were derived. In order to achieve this level of selectivity, given the large number of ion detections at any given moment of a liquid chromatography separation, an orthogonal pre-ion detection separation technique such as ion mobility separation may be used.

In quantitative experiments accurate and precise measures of abundance by peak volume is a direct consequence of how well the physico-chemical attributes of each eluting compound is measured. Similarly, in qualitative experiments the selectivity of identification relative to the sheer number of possibilities is also a direct consequence of how well these attributes are measured.

It is known to operate a mass spectrometer in either a Data Dependent Acquisition mode of operation or a Data Independent Acquisition mode of operation.

In a Data Dependent Acquisition mode of operation fragment or product ions are formed from parent or precursor ions that are mass resolved (using a quadrupole mass filter isolation window). In contrast, in a Data Independent Acquisition mode of operation fragment or product ions are formed from parent or precursor ions that are either time resolved ($MS^E$) or time and ion mobility drift time resolved (HD-$MS^E$).

With respect to Data Dependent Acquisitions ("DDA") sensitivity, as defined by accessing the lower end of the experimental dynamic range, is a function of time given there is a minimum parent or precursor ion intensity to produce a sufficient number of fragment or product ions in order to facilitate a valid identification. However, due to the compromising nature of conventional serial Data Dependent Acquisition methods the duty cycle is proportional to the acquisition time and the sensitivity is inversely proportion to duty cycle.

With respect to chimeracy, Data Dependent Acquisition methods utilise an ion selection window whereby only parent or precursor ions present within the selection window are transferred to the collision cell. Sensitivity is inversely proportional to the width of the isolation window. Given the complexity of complex systems in order to retain any semblance of sensitivity rarely, if ever, will there exist just a single parent or precursor ion within an isolation window.

By way of contrast, with Data Independent Acquisition ("DIA") sensitivity is not compromised given there is no partial peak sampling. Data is acquired on each and every parent or precursor ion throughout its chromatographic elution. However, Data Independent Acquisition methods are prone to suffer from the problem of chimeracy.

The adverse effects of chimeracy can be mitigated through the use of an additional in-line orthogonal ion mobility separation. Accordingly, as with Data Dependent Acquisition methods when analysing complex systems there will normally be a plurality of parent or precursor ions that potentially represent any aligned fragment or product ions. In contrast to Data Dependent Acquisition, the inflexion point is not a function of sensitivity. It is, however, a function of chimeracy.

Both conventional acquisition methods therefore suffer from various problems that limit clarity and depth of coverage in the analysis of complex systems.

In order to further illustrate the problem, the sheer complexity and dynamic range of complex systems will be considered in more detail. The lack of diversity of biomolecules in terms of their elemental composition will also be discussed in more detail below.

A detailed examination of proteins and proteomes reveals a very high degree of similarity in amino acid composition. It is reasonable to assume that on average the number of peptides generated from an enzymatic digestion of a protein is a direct consequence of length. If the amino acid composition is similar and the number of peptides generated is a function of length then it is reasonable to assume that many peptides from multiple proteins will have similar elemental compositions. Similar elemental compositions will restrict the number of available mass to charge ratio values as well as elution space and, if ion mobility spectrometry ("IMS") is employed then also cross-sectional area.

Overwhelmingly, all bio-molecules are comprised of six elements (C, N, H, O, S, and P). With this being the case, ~40% of all available space in terms of mass to charge ratio can never be occupied by a biomolecule. More specifically, within a one mass unit window there are four Gaussian distributions each ~120 mDa wide. Summing the centered count of these distributions reveals that ~40% of all naturally occurring biomolecules acquired at 40,000 mass resolving power occupy only 10% of the available mass to charge ratio space. In addition, the experimental dynamic range of a typical sample typically spans ~3-3.5 orders of magnitude. Unfortunately, ~66.6% of all ion detections reside in the last order of magnitude with ~50% in the last half order. As such, ~60% of all ion detections will have similar mass to charge ratios and will also reside at the lowest levels of sensitivity. Given the lack of elemental diversity and the similarity in mass to charge ratio it may be assumed that the distribution of ion detections across a gradient elution follows a Gaussian distribution with the highest density representing the most common elemental composition.

J. Egertson, A. Kuehn, G. Merrihew, N. Bateman, B. MacLean, Y. Ting, J. Canterbury, D. Marsh, M. Kellmann, V. Zabrouskov, C. Wu and M. MacCoss "Multiplexed MS/MS for Improved Data Independent Acquisition" Nat. Methods August (2013) discloses a multiplexing strategy (MSX) wherein five separate 4 m/z isolation windows are analysed per spectrum. These spectra are demultiplexed into the five separate 4 m/z isolation windows using a strategy with similarities to Hadamard multiplexing resulting in data with the sampling frequency of a Data Independent Acquisition approach using 20×20 m/z wide windows but the selectivity of an approach using 100×4 m/z wide windows.

It is desired to provide an improved method of mass spectrometry.

SUMMARY

According to an aspect there is provided a method of mass spectrometry comprising:

ionising a sample eluting from a separation device in order to generate a plurality of parent ions; and performing multiple cycles of operation as the sample elutes from the separation device, wherein each cycle of operation comprises the steps of:

(i) mass analysing the parent ions to obtain parent ion mass spectral data;

(ii) transmitting the parent ions to a fragmentation or reaction device without substantially mass filtering the parent ions, causing the parent ions to fragment or react to form fragment or product ions and obtaining fragment or product ion mass spectral data;

(iii) mass filtering the parent ions so that first parent ions having mass to charge ratios within a first mass to charge ratio range are onwardly transmitted to a fragmentation or reaction device, causing the first parent ions to fragment or react to form first fragment or product ions and obtaining first fragment or product ion mass spectral data; and (iv) mass filtering the parent ions so that second parent ions having mass to charge ratios within a second different mass to charge ratio range are onwardly transmitted to a fragmentation or reaction device, causing the second parent ions to fragment or react to form second fragment or product ions and obtaining second fragment or product ion mass spectral data.

In embodiments, each cycle of operation may further comprise the step of (v) mass filtering the parent ions so that third parent ions having mass to charge ratios within a third different mass to charge ratio range are onwardly transmitted to a fragmentation or reaction device, causing the third parent ions to fragment or react to form third fragment or product ions and obtaining third fragment or product ion mass spectral data. Each cycle of operation may further comprise the step of (vi) mass filtering the parent ions so that fourth parent ions having mass to charge ratios within a fourth different mass to charge ratio range are onwardly transmitted to a fragmentation or reaction device, causing the fourth parent ions to fragment or react to form fourth fragment or product ions and obtaining fourth fragment or product ion mass spectral data. Each cycle of operation may further comprise the step of (vii) mass filtering the parent ions so that fifth parent ions having mass to charge ratios within a fifth different mass to charge ratio range are onwardly transmitted to a fragmentation or reaction device, causing the fifth parent ions to fragment or react to form fifth fragment or product ions and obtaining fifth fragment or product ion mass spectral data. Each cycle of operation may further comprise the step of (viii) mass filtering the parent ions so that sixth parent ions having mass to charge ratios within a sixth different mass to charge ratio range are onwardly transmitted to a fragmentation or reaction device, causing the sixth parent ions to fragment or react to form sixth fragment or product ions and obtaining sixth fragment or product ion mass spectral data. Each cycle of operation may further comprise the step of (ix) supplying and/or mass analysing lockmass or calibration ions in order to check and/or adjust a mass to charge ratio calibration of a mass spectrometer.

In embodiments, steps (i) and (ii) may comprise a Data Independent Acquisition mode of operation and/or steps (iii)-(viii) may comprise a Data Dependent Acquisition mode of operation.

In embodiments, the method may further comprise determining the mass to charge ratios of parent ions from the parent ion mass spectral data. The step of mass filtering the parent ions may comprise setting the mass to charge ratio transmission window of a mass filter so as to onwardly transmit parent ions having a mass to charge ratio which corresponds with a mass to charge ratio of parent ions determined to be present in the parent ion mass spectral data. The step of mass filtering the parent ions may comprise setting the mass to charge ratio transmission window of a mass filter so as to attenuate other ions which do not correspond with the parent ions determined to be present in the parent ion mass spectral data.

In embodiments, the duration of each cycle of operation may be selected from the group consisting of: (i) <about 0.5 s; (ii) about 0.5-1 s; (iii) about 1-1.5 s; (iv) about 1.5-2 s; (v) about 2-2.5 s; (vi) about 2.5-3 s; and (vii) >about 3 s.

In embodiments, during step (i) parent ions may not be substantially subjected to fragmentation or reaction.

In embodiments, step (i) may be performed prior to or subsequent to step (ii) during at least some or substantially all cycles of operation. Step (i) and/or step (ii) may be performed prior to or subsequent to step (iii) and/or step (iv) and/or step (v) and/or step (vi) and/or step (vii) and/or step (viii) and/or step (ix) during at least some or substantially all cycles of operation.

In embodiments, the intensity of fragment or product ions having a particular mass to charge ratio may be determined from summing the intensity of the fragment or product ions from the fragment or product ion mass spectral data and/or the first fragment or product ion mass spectral data and/or the second fragment or product ion mass spectral data and/or the third fragment or product ion mass spectral data and/or the fourth fragment or product ion mass spectral data and/or the fifth fragment or product ion mass spectral data and/or the sixth fragment or product ion mass spectral data.

In embodiments, step (i) and/or step (ii) and/or step (iii) and/or step (iv) and/or step (v) and/or step (vi) and/or step (vii) and/or step (viii) and/or step (ix) may further comprise separating the parent ions and/or fragment or product ions according to their ion mobility or differential ion mobility.

In embodiments, the first mass to charge ratio range and/or the second mass to charge ratio range and/or the third mass to charge ratio range and/or the fourth mass to charge ratio range and/or the fifth mass to charge ratio range and/or the sixth mass to charge ratio range may have a width <about 0.5 Da, about 0.5-1.0 Da, about 1.0-1.5 Da, about 1.5-2.0 Da, about 2.0-2.5 Da, about 2.5-3.0 Da, about 3.0-3.5 Da, about 3.5-4.0 Da, about 4.0-4.5 Da, about 4.5-5.0 Da or >about 5.0 Da. Alternatively, the first mass to charge ratio range and/or the second mass to charge ratio range and/or the third mass to charge ratio range and/or the fourth mass to charge ratio range and/or the fifth mass to charge ratio range and/or the sixth mass to charge ratio range may have a width <about 5 Da, about 5-10 Da, about 10-15 Da, about 15-20 Da, about 20-25 Da, about 25-30 Da, about 30-35 Da, about 35-40 Da, about 40-45 Da, about 45-50 Da or >about 50 Da.

In embodiments, the sample may comprise a biological, organic, inorganic, chemical or pharmaceutical sample. The sample may comprise a complex mixture of biomolecules or organic molecules.

The method according to an embodiment may address the problem of sensitivity and chimeracy.

An embodiment relates to a system and a method for enhancing parent or precursor ion and product ion alignment. The method may enable highly selective targeted analyses to be performed.

The method may be transparent to sample source and can work on substantially all sample types.

An embodiment represents an improvement over conventional analytical approaches and at one level can be considered to comprise a hybrid of a Data Dependent Acquisition ("DDA") approach and a Data Independent Acquisition ("DIA") approach. Conventional Data Independent Acquisition methods include $MS^E$ and $HD-MS^E$ methodologies. The difference between $MS^E$ and $HD-MS^E$ methodologies is that the known $HD-MS^E$ methodology additionally includes the step of separating ions temporally according to their ion mobility in an ion mobility spectrometer or separator.

Fragment or product ions which are detected in a Data Dependent Acquisition spectrum must also be present in a corresponding Data Independent Acquisition fragment or product ion spectrum.

In a Data Dependent Acquisition mode of operation, fragment or product ions are formed from parent or precursor ions that are mass resolved (using a quadrupole mass filter isolation window) whereas in a Data Independent Acquisition fragment or product ions are formed from parent or precursor ions that are time resolved ($MS^E$) or time and ion mobility drift resolved ($HD-MS^E$).

The difference in how parent or precursor ions are resolved prior to Collision Induced Dissociation fragmentation provides the necessary orthogonality in order to align parent or precursor ions with their corresponding or companion product or fragment ions. The enhancement in ion alignment according to an embodiment provides the necessary increase in selectivity to facilitate the searching of every large search space with exceedingly high selectivity.

As with most, if not all, analytical methodologies there is some degree of trade-off or compromise. Due to the serial nature of a Data Dependent Acquisition experimental duty cycle, the number of MS/MS spectra which are acquired is a direct consequence of acquisition time. Sensitivity is inversely proportional to acquisition time and the width of the parent or precursor isolation window. Narrower parent or precursor isolation windows limit the number of parent or precursor ions entering the collision cell. Although reducing the number of chimeric events (i.e. number of co-fragmenting parent or precursor ions) is advantageous, narrow isolation windows reduce sensitivity which is problematic. As such, given the complexity of these systems, in order to retain any semblance of sensitivity rarely if ever will there be a single parent or precursor ion within an isolation window.

With respect to Data Independent Acquisitions ("DIA"), sensitivity is not compromised since there is no partial peak sampling. Data is acquired on each and every parent or precursor ion throughout its chromatographic elution. However, Data Independent Acquisitions suffer from the problem of chimeracy. The adverse effects of chimeracy can be mitigated through the use of an additional in-line orthogonal ion mobility separation stage. Thus as with Data Dependent Acquisition, when analysing complex systems, there will nearly always be a plurality of candidate parent or precursor ions that could potentially be associated with any given fragment or product ion.

Both conventional acquisition methods suffer from problems which limits clarity and depth of coverage in the analysis of complex systems.

According to an embodiment a hybrid (e.g. DIA-DDA) method may be utilised.

According to an embodiment a mass spectrometer comprising a highly efficient stacked ring ion guide may be used to transmit ions so that mass spectral data may be acquired which is of similar quality to other conventional mass spectrometers but at $\frac{1}{10}^{th}$ of the on-column load.

The significant increase in ion transfer efficiency which is afforded by the use of stacked ring ion guides enables data acquisition at higher mass resolving powers to be performed and provides additional time for interspersing Data Dependent Acquisition acquisitions with $MS^E$ or $HD-MS^E$ Data Independent Acquisitions with no significant reduction in sensitivity.

With respect to selective targeted experiments an include list of mass to charge ratio and retention times of known molecular components expected to be present in the sample may be used for targeted MS/MS acquisitions. Given the specificity of an example workflow, the size of the mass to charge ratio isolation window may be increased to capture more targets per MS/MS acquisition given the complementary time and/or time and drift aligned ion lists in conjunction with the fact that it is known what the fragment ions are for each target.

During data reduction each parent or precursor ion selected for MS/MS may be found in the low-energy (non-fragmentation) MS data. The parent or precursor isolation width may then be applied and all concurrently fragmenting parent or precursor ions may be assigned the same product ions as the selected parent or precursor.

The mass resolved fragment or product ions may then be intersected with the time and/or time and ion mobility drift time resolved fragment or product ions from $MS^E$ or $HD-MS^E$ acquisitions and only the ions in common are retained in the Data Dependent Acquisition parent or precursor and product ion list. The intensities of the matched ions may then be summed with the $MS^E$ or $HD-MS^E$ variants removed from the time and/or time and ion mobility drift time resolved parent or precursor/product ion lists. Summing the intensities increases the sensitivity of the Data Dependent Acquisition experiments whilst removal of the matched fragment or product ions reduces the chimeracy of the $MS^E$ or $HD-MS^E$ experiments. Correctly implemented fragment or product ions will only be assigned to parent or precursor ions within the mass isolation window exhibiting the same center mass retention-time and, if ion mobility separation is employed, center mass retention and drift times within the user defined match tolerances.

The method according to an embodiment provides the means to increase clarity and depth of coverage in complex systems by maximizing both the sensitivity and selectivity of the employed workflow. Enhanced selectivity (peak capacity) may enable the method to measure the physico-chemical attributes of each ion independent of all others.

An embodiment is particularly advantageous in that the ability to accurately align parent or precursor ions and corresponding fragment or product ions may afford the method the ability to query exceedingly large search spaces for both chemical and post-translational modifications as well as point mutants and truncations with a higher degree of specificity. Accordingly, mass spectral data produced according to an embodiment enables substantially improved qualitative and quantitative results to be obtained compared to conventional techniques.

According to another aspect there is provided a mass spectrometer comprising:

an ion source arranged and adapted to ionise a sample eluting from a separation device in order to generate a plurality of parent ions; and a control system arranged and adapted to perform multiple cycles of operation as the sample elutes from the separation device, wherein each cycle of operation comprises the steps of:

(i) mass analysing the parent ions to obtain parent ion mass spectral data;

(ii) transmitting the parent ions to a fragmentation or reaction device without substantially mass filtering the parent ions, causing the parent ions to fragment or react to form fragment or product ions and obtaining fragment or product ion mass spectral data;

(iii) mass filtering the parent ions so that first parent ions having mass to charge ratios within a first mass to charge ratio range are onwardly transmitted to a fragmentation or reaction device, causing the first parent ions to fragment or react to form first fragment or product ions and obtaining first fragment or product ion mass spectral data; and (iv) mass filtering the parent ions so that second parent ions having mass to charge ratios within a second different mass to charge ratio range are onwardly transmitted to a fragmentation or reaction device, causing the second parent ions to fragment or react to form second fragment or product ions and obtaining second fragment or product ion mass spectral data.

According to another aspect there is provided a method of mass spectrometry comprising:

ionising a sample eluting from a separation device in order to generate a plurality of parent ions; and performing multiple cycles of operation as the sample elutes from the separation device, wherein each cycle of operation comprises the steps of:

(i) mass analysing the parent ions to obtain parent ion mass spectral data;

(ii) transmitting the parent ions to a fragmentation or reaction device without substantially mass filtering the parent ions, causing the parent ions to fragment or react to form fragment or product ions and obtaining fragment or product ion mass spectral data;

(iii) mass filtering the parent ions so that first parent ions having mass to charge ratios within a first mass to charge ratio range are onwardly transmitted to a fragmentation or reaction device, causing the first parent ions to fragment or react to form first fragment or product ions and obtaining first fragment or product ion mass spectral data; and (iv) mass filtering the parent ions so that second parent ions having mass to charge ratios within a second different mass to charge ratio range are onwardly transmitted to a fragmentation or reaction device, causing the second parent ions to fragment or react to form second fragment or product ions and obtaining second fragment or product ion mass spectral data;

wherein the step of mass filtering the parent ions comprises setting the mass to charge ratio transmission window of a mass filter so as to onwardly transmit parent ions having a mass to charge ratio which corresponds with a mass to charge ratio of parent ions determined to be present in the parent ion mass spectral data.

According to another aspect there is provided a mass spectrometer comprising:

an ion source arranged and adapted to ionise a sample eluting from a separation device in order to generate a plurality of parent ions; and a control system arranged and adapted to perform multiple cycles of operation as the sample elutes from the separation device, wherein each cycle of operation comprises the steps of:

(i) mass analysing the parent ions to obtain parent ion mass spectral data;

(ii) transmitting the parent ions to a fragmentation or reaction device without substantially mass filtering the parent ions, causing the parent ions to fragment or react to form fragment or product ions and obtaining fragment or product ion mass spectral data;

(iii) mass filtering the parent ions so that first parent ions having mass to charge ratios within a first mass to charge ratio range are onwardly transmitted to a fragmentation or reaction device, causing the first parent ions to fragment or react to form first fragment or product ions and obtaining first fragment or product ion mass spectral data; and (iv) mass filtering the parent ions so that second parent ions having mass to charge ratios within a second different mass to charge ratio range are onwardly transmitted to a fragmentation or reaction device, causing the second parent ions to fragment or react to form second fragment or product ions and obtaining second fragment or product ion mass spectral data;

wherein the control system is further arranged and adapted so that the step of mass filtering the parent ions comprises setting the mass to charge ratio transmission window of a mass filter so as to onwardly transmit parent ions having a mass to charge ratio which corresponds with a mass to charge ratio of parent ions determined to be present in the parent ion mass spectral data.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage may have an amplitude selected from the group consisting of: (i)<about 50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i)<about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i)<about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described together with other arrangements given for illustrative purposes only, by way of example only, and with reference to the accompanying drawings in which:

FIG. 3 illustrates an embodiment wherein one low energy scan, one high energy scan followed by six DDA scans are performed every cycle, wherein each cycle lasts approximately 1.5 s;

FIG. 4B shows how a cycle may comprise a low energy acquisition and a high energy acquisition followed by six Data Dependent Acquisitions ("DDA") scans, wherein each cycle may last 1.5 s and FIG. 4C shows six Data Dependent Acquisitions which may be performed each cycle and wherein according to an embodiment eight cycles may be performed across the FWHM of an ion peak measured as a function of chromatographic retention time;

FIG. 6A shows two DIA channels of a nine channel precursor ion discovery ("PID") acquisition according to an embodiment and FIG. 6B shows six DDA channels of a nine channel precursor ion discovery ("PID") acquisition according to an embodiment.

DETAILED DESCRIPTION

Some of the issues associated with the complexity of samples and the dynamic range in the analysis of complex systems will first be discussed and illustrated below utilising real experimental data.

Experimental data was obtained using 5 µg of MDA-MB-231 breast cancer cells which were lysed, reduced, alkylated and enzymatically digested with trypsin. 500 ng of the resulting polypeptide pool was then separated over 60 minutes using a 25 cm BEH column coupled to a SYNAPT® G2-Si mass spectrometer which was arranged to operate in $MS^E$, $HD-MS^E$ and top 10 Data Dependent Acquisition modes of operation.

Figure 1A:
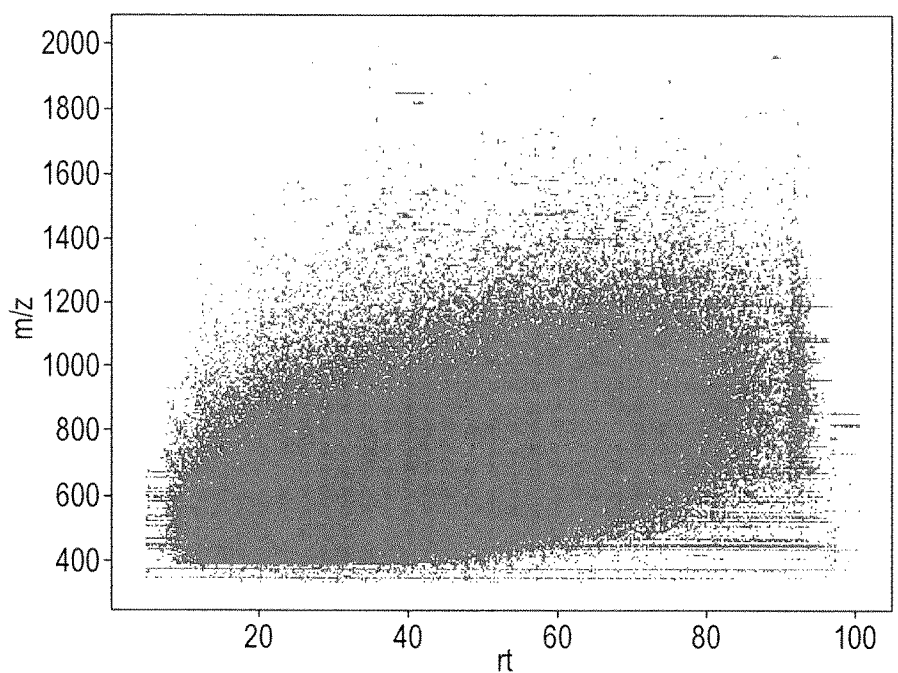
FIG. 1A shows a scatter plot of mass to charge ratio versus retention-time relating to 551,000 HD-MS$^E$ ion detections.

FIGS. 1A-1 illustrate a series of scatter plots, bar charts and histograms validating the theoretical descriptions of dynamic range, mass to charge ratio, chromatographic retention time and ion mobility drift times, as well as peak widths (FWHM) in mass to charge ratio, chromatographic retention time and ion mobility drift time.

Post-acquisition processing revealed ~332,000 (332 k) low-energy ion detections when the mass spectrometer was operated in a $MS^E$ mode of operation. When the mass spectrometer was operated in a $HD-MS^E$ mode of operation wherein ions were also separated according to their ion mobility then ~551,000 (551 k) ion detections were revealed. The data reported is from the same loading of the sample and the sample was separated using the same gradient.

The additional 200,000+ ion detections in the $HD-MS^E$ mode of operation were present in the $MS^E$ analysis but the potential ion detections were hidden by other ions due to co-elution effects. The inclusion of the additional orthogonal separation afforded by the ion mobility separator allows not only for these additional ions to be detected but also for the physico-chemical attributes of all ions to be measured independent of the surrounding matrix.

The method may allow for constant acquisition until an ion of interest is observed then the target is switched ON, resulting companion, product or fragment ion lists compared and the target validated. Increasing the size of the net in proportion to the sample complexity allows for more ions of interest to be selected for concurrent MS/MS acquisition. Given the uncompromising nature of the data-independent side of the workflow, according to an embodiment the processed data can be re-screened as additional validate biomarkers are discovered.

The workflow according to an embodiment is sample independent and is beneficial across all the verticals. The workflow is entirely transparent to the sample source. The data reduction method is the same irrespective of the size of the molecules being analysed. The acceptable degrees of freedom afforded by the sample type will determine mass resolution, gradient length, use of ion mobility separation and whether or not to include multi-level fractionation.

FIG. 1A shows a scatter plot illustrating mass to charge ratio versus chromatographic retention time in respect of the 551,000 $HD-MS^E$ ion detections.

Figure 1B:
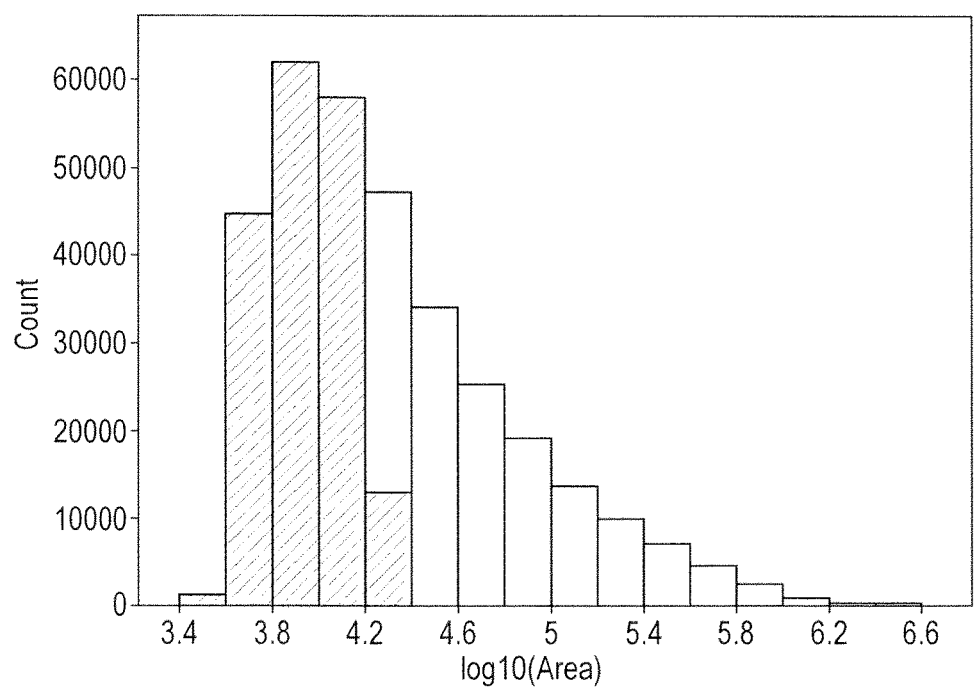
FIG. 1B illustrates the dynamic range.

FIG. 1B illustrates the experimental dynamic range. It is presumed that the upper end of the dynamic range is being under represented due to the saturation effects afforded by the higher intensity ions.

Figure 1C:
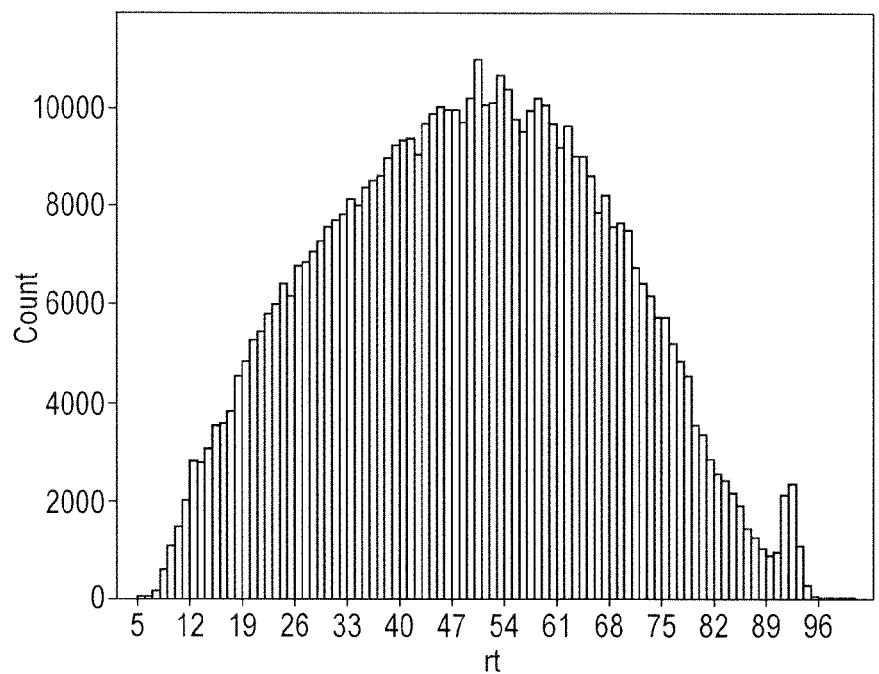
FIG. 1C shows the count of ions per unit time in 1 min time bins of chromatographic retention time.

FIGS. 1C-F illustrate the effects of the lack of elemental diversity in the construction of biomolecules. FIG. 1C shows the count of ions per unit time in 1 min chromatographic retention time bins and illustrates a wide Gaussian distribution reflecting ~200 ion detections/second at its apex. Similarity in hydrophobicity suggests a similarity in composition which is validated in FIGS. 1D and 1E.

Figure 1D:
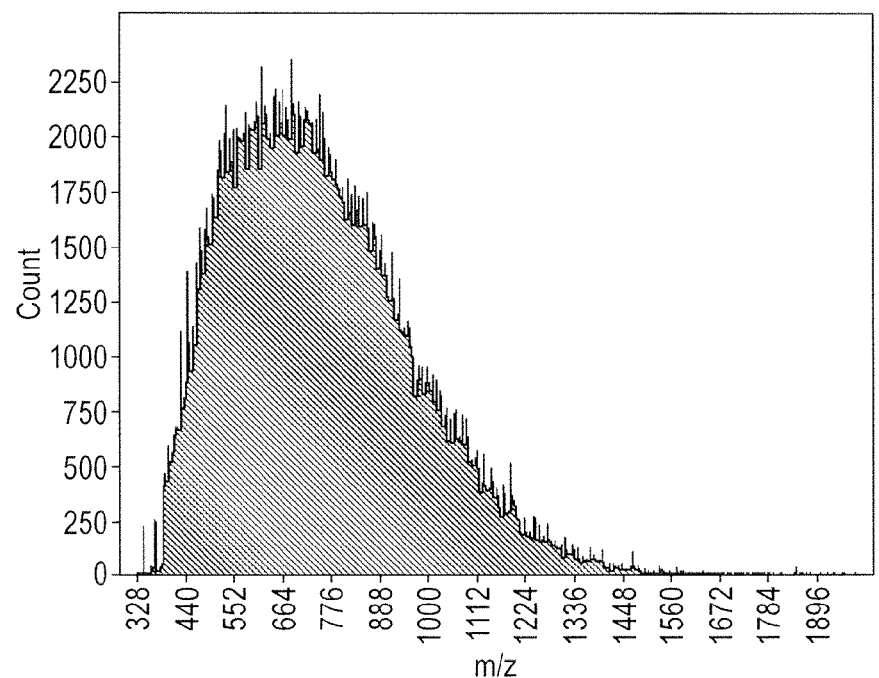
FIG. 1D shows the count of mass to charge ratio in 2 Da bins.
Figure 1E:
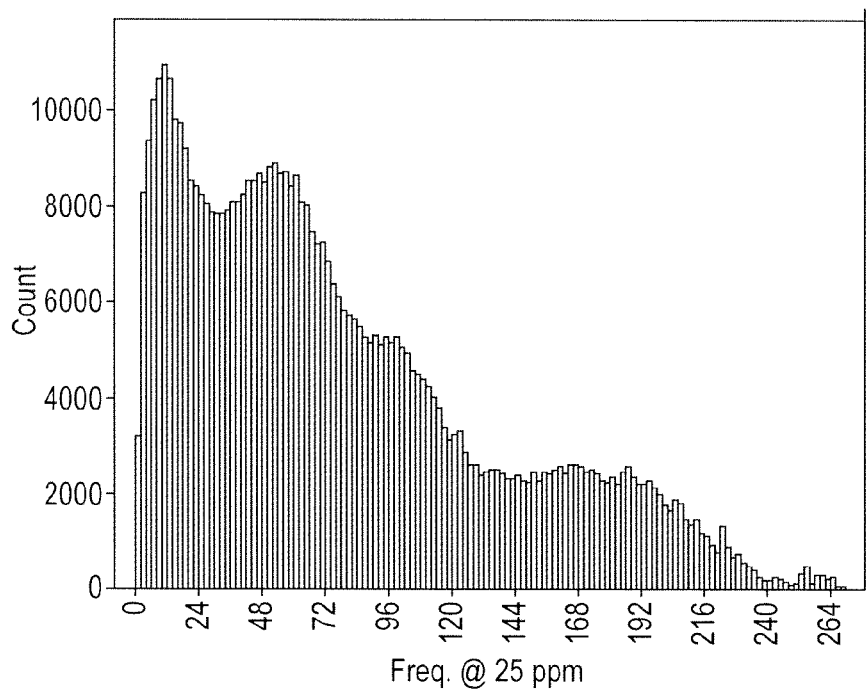
FIG. 1E shows the count of the frequency of mass to charge ratio at 25 ppm.
Figure 1F:
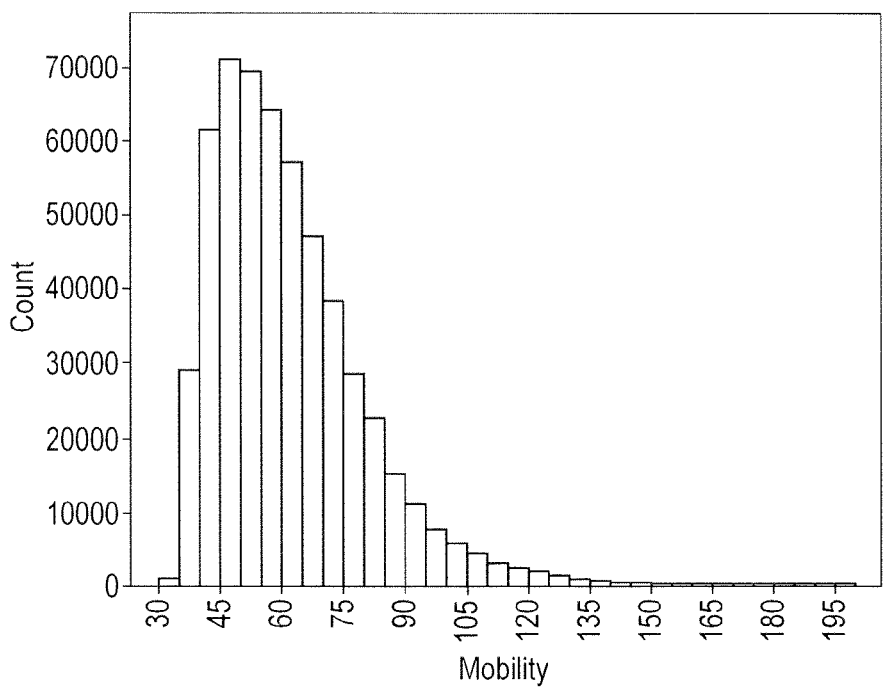
FIG. 1F shows the distribution of ion mobility drift time $t_{drift}$.

FIG. 1D illustrates the distribution of mass to charge ratio in 2 Dalton windows and FIG. 1E illustrates the selectivity of each at 25 ppm. Both graphs cast doubt on the specificity of an exact mass measurement alone when it comes to the analysis of complex systems.

Figure 1G:
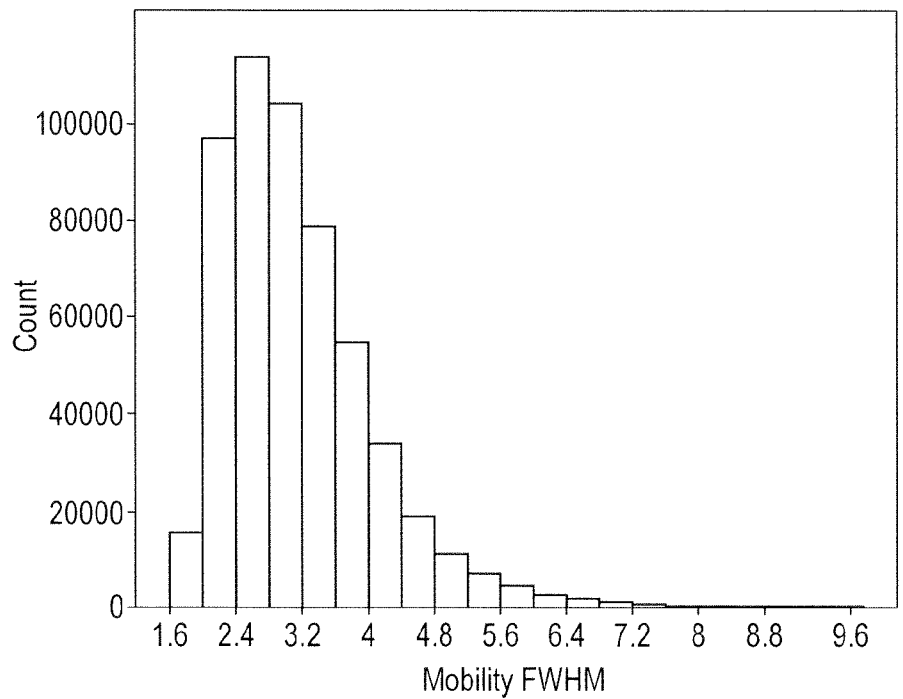
FIG. 1G shows the distribution of ion mobility drift FWHM.

Although there are 200 drift lanes (i.e. ion mobility drift time channels) available in a conventional $HD-MS^E$ workflow, due to lack of elemental diversity, as illustrated by FIG. 1G, there is a limited Gaussian distribution occupying about half of the available ion mobility separation space. Although limited in accessing the available drift space, the addition of the ion mobility separation was nonetheless important in unearthing an additional 200,000+ ions as well as providing the selectivity to ensure the measurement accuracy of both their physico-chemical attributes as well as the others that they were interfering with.

Figure 1H:
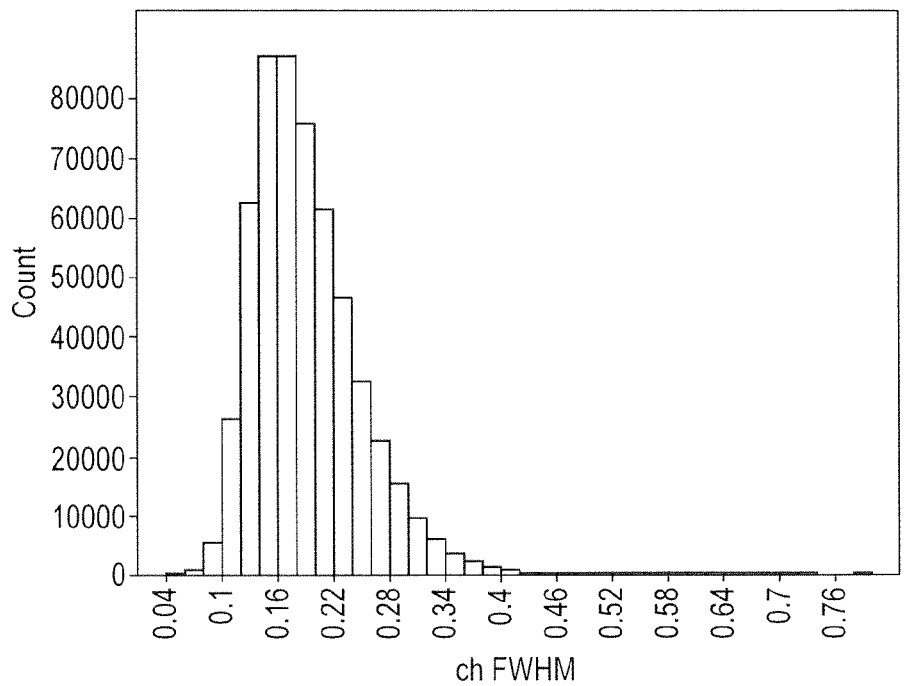
FIG. 1H shows the distribution of chromatographic ion peak FWHM and FIG. 1I shows the distribution of the effective mass resolving power $R_{s\ effective}$.
Figure 1I:
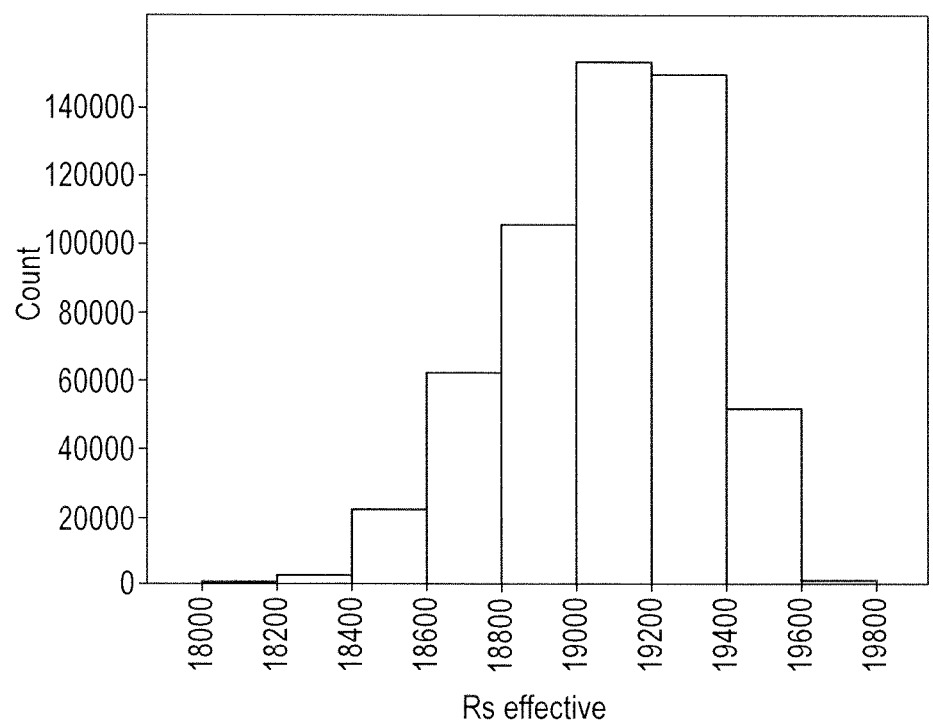

FIGS. 1G-I illustrate the selectivity of each of the three available orthogonal separation techniques.

In Data Independent Acquisitions, data is acquired continuously in an alternating fashion (i.e. low collision energy/ high collision energy) across the entire gradient elution allowing the ion detection method to measure the width at half-height of all ion detections in each of the three dimensions of chromatographic retention time, ion mobility drift time and mass to charge ratio.

FIG. 1H shows a very tight distribution of chromatographic peak widths centered at ~12 seconds. Narrow peaks provide for greater peak capacity and higher ion flux providing for both greater selectivity and sensitivity.

With respect to mass resolving power, FIG. 1I illustrates the distribution of the effective mass resolution. The effective mass resolution $R_{s\ effective}$ is calculated by dividing the measured mass to charge ratio of each ion by its calculated half-height. The fact that the center of the distribution is very similar to that of unencumbered lock mass further clarifies the importance of ion mobility separation in providing the additional selectivity necessary to ensure that the physico-chemical attributes of each ion are measured independent of all others.

With respect to the selectivity of ion alignment, both isotopes to charge clusters as well as product ions to parent or precursor ions, FIGS. 2A-D exemplifies the selectivity of various different conventional workflows. FIGS. 2E-H illustrate hybrid workflows according to embodiments. For enhanced clarity the x and y-axis for all plots (apart from the $MS^E$ plot shown in FIG. 2C) are scaled equally.

The x-axis represents the number of ions contained within the noted bin tolerances and the y-axis expresses the count of the number of times that ions in a particular tolerance bin are presented in the data. Given that a single eluting compound (molecule) when ionised exists as a series of isotopes, the number and distribution of which is directly proportional to its elemental composition and concentration, all eluting biomolecules will exist in the mass analyser as a series of isotopes. As such, the count reflected in each of the histograms does not reflect the total number of co-eluting compounds. Assuming an average of four isotopes per charge group then the number of co-eluting compounds would be equal to the ion count divided by four.

For simplicity, plots illustrating very narrow distributions at the lower end of the x-axis as shown, for example, in FIGS. 2E-2H illustrate the highest selectivity. It is apparent that the approach according to an embodiment as illustrated by FIGS. 2E-2H results in a significant improvement in selectivity compared to current state of the art approaches (which are illustrated by FIGS. 2A-2D and which suffer from a relatively low selectivity in comparison).

Given that the sensitivity of each workflow is not taken into account in the binning process, care should be taken when interpreting the experimental results shown in FIGS. 2A-F.

Figure 2A:
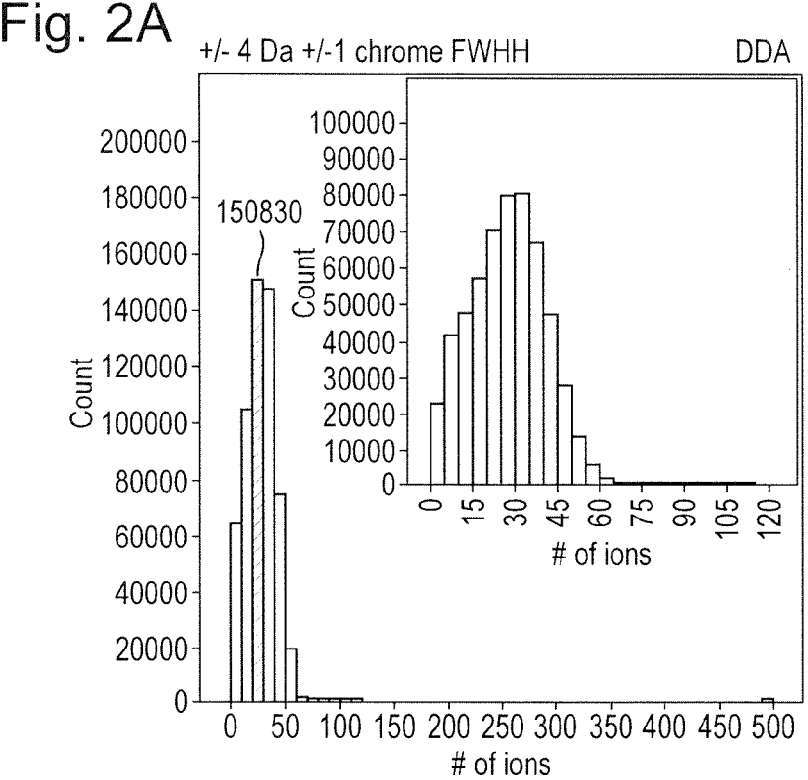
FIG. 2A shows the ion density distribution of a Data Dependent Acquisition acquired using ±4 Da mass isolation window and requiring a ±1 median chromatographic peak width FWHM.

FIG. 2A shows the ion density distribution of a typical conventional Data Dependent Acquisition experiment employing a +/−4 Dalton mass isolation window and a center mass retention time tolerance window of +/−1× the time associated with the median chromatographic peak width.

It should be noted that a known problem with Data Dependent Acquisition methodologies is sensitivity. Given a typical chromatographic peak width at half height of 12 s and a 50 ms MS/MS acquisition time then only 1/240 of the peaks' volume will be sampled. In addition, on average the relative intensity of the most abundant fragment or product ion is at best 25% that of the corresponding parent or precursor ion. Given that it is not possible to confidently identify a biomolecule without observing corresponding characteristic fragment or product ions, the true sampling volume is ~1/1000$^{th}$ of the available peak volume. The adverse effect of the compromised sensitivity is illustrated by the hatched bars in FIG. 1B. The hatched bars represent the parent or precursor ions that are not available for Data Dependent Acquisition analysis. Though the number of available ions is reduced by half, there still exists 250 k+ ions available for qualitative identification.

Figure 2B:
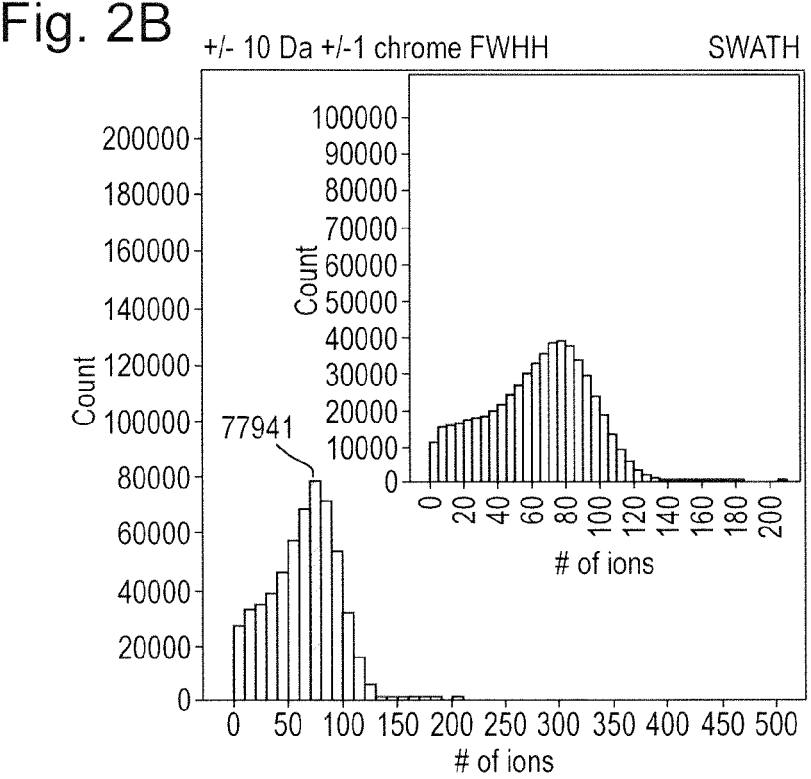
FIG. 2B shows the ion density distribution from a SWATH acquisition acquired using a ±10 Da mass isolation window and requiring a ±1 median chromatographic peak width FWHM.

FIG. 2B demonstrates how the width of the isolation window affects the selectivity of the Data Dependent Acquisition experiment. While increasing the width of the isolation window in order to implement a SWATH acquisition creates a greater concurrence of fragmenting parent or precursor ions, the increase in width also allows for longer acquisition times. Data Dependent Acquisition results in a compromise involving sensitivity, duty cycle and chimeracy.

Figure 2C:
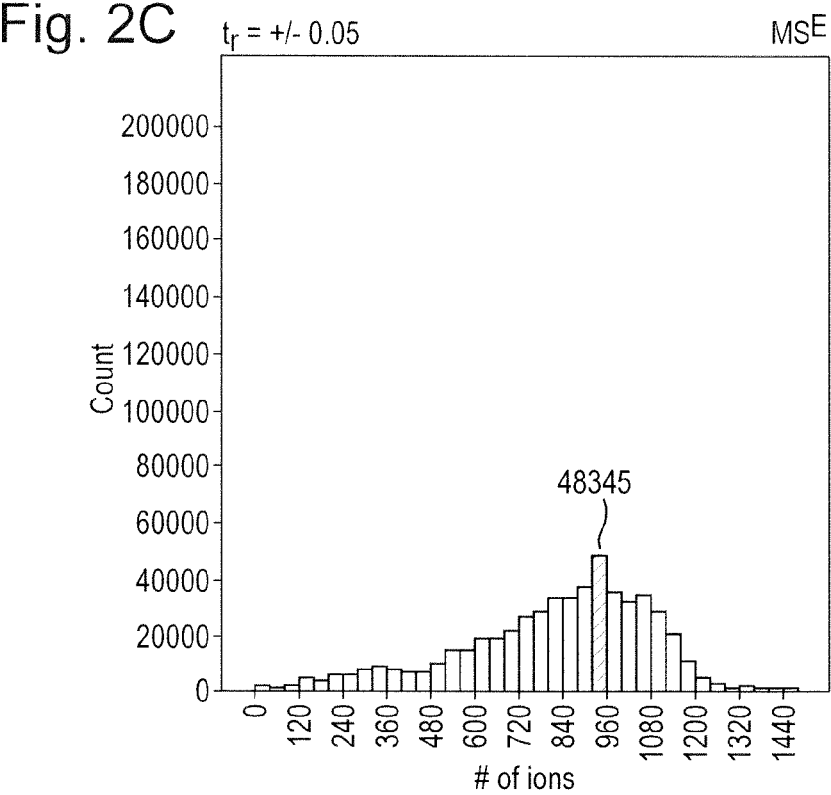
FIG. 2C shows the ion density distribution from a MS$^E$ acquisition acquired with the chromatographic retention time $t_r$=±0.05.
Figure 2D:
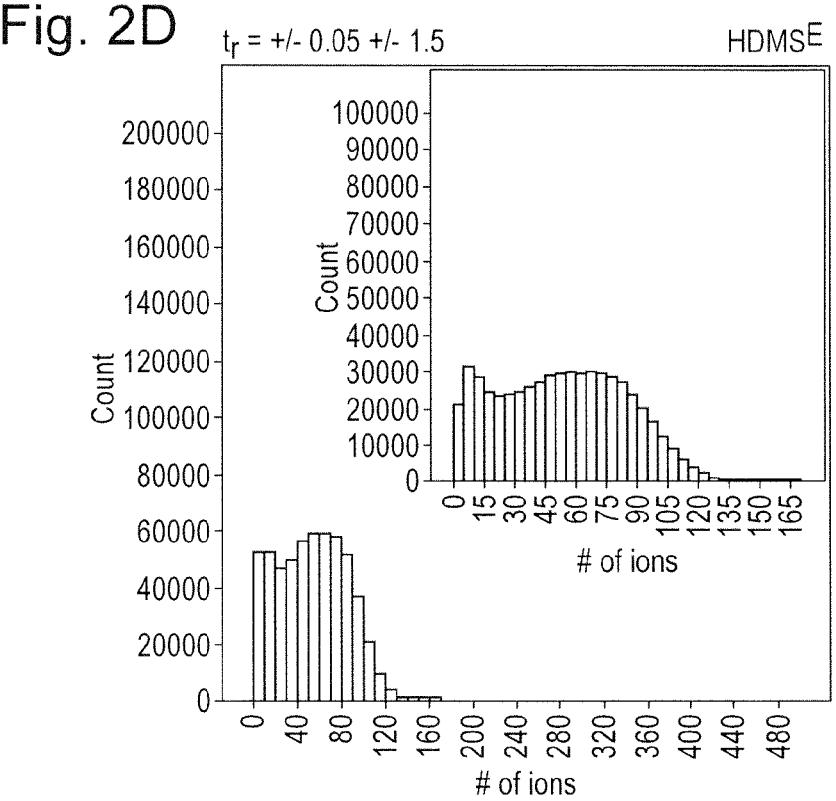
FIG. 2D shows the ion density distribution from a HD-MS$^E$ acquisition with the chromatographic retention time $t_r$=±0.05 and requiring an ion mobility drift time of ±1.5.
Figure 2E:
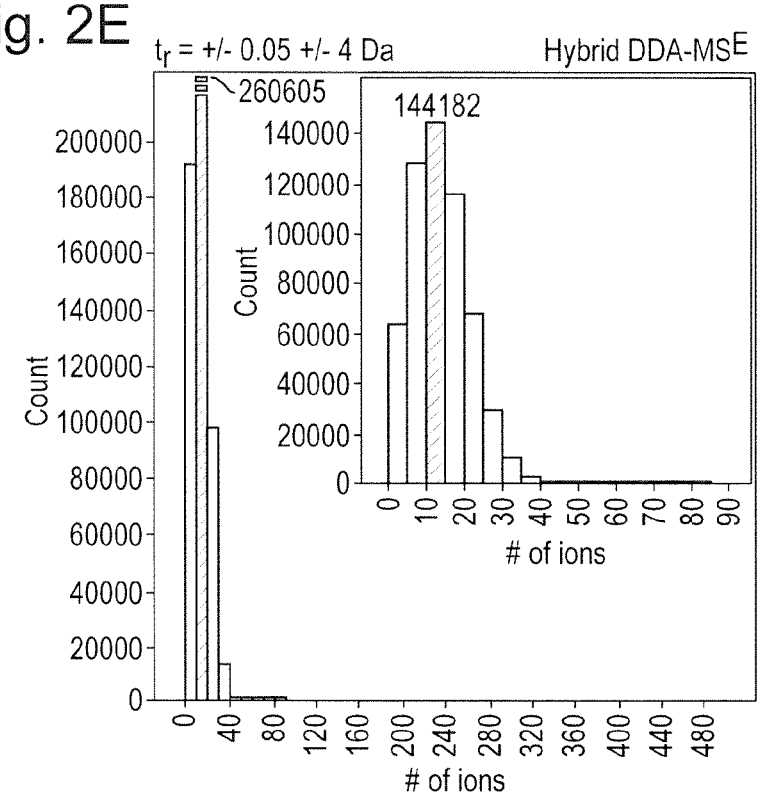
FIG. 2E shows the ion density distribution from a hybrid DDA-MS$^E$ acquisition according to an embodiment wherein the chromatographic retention time $t_r$=±0.05 and a ±4 Da mass isolation window was used.
Figure 2F:
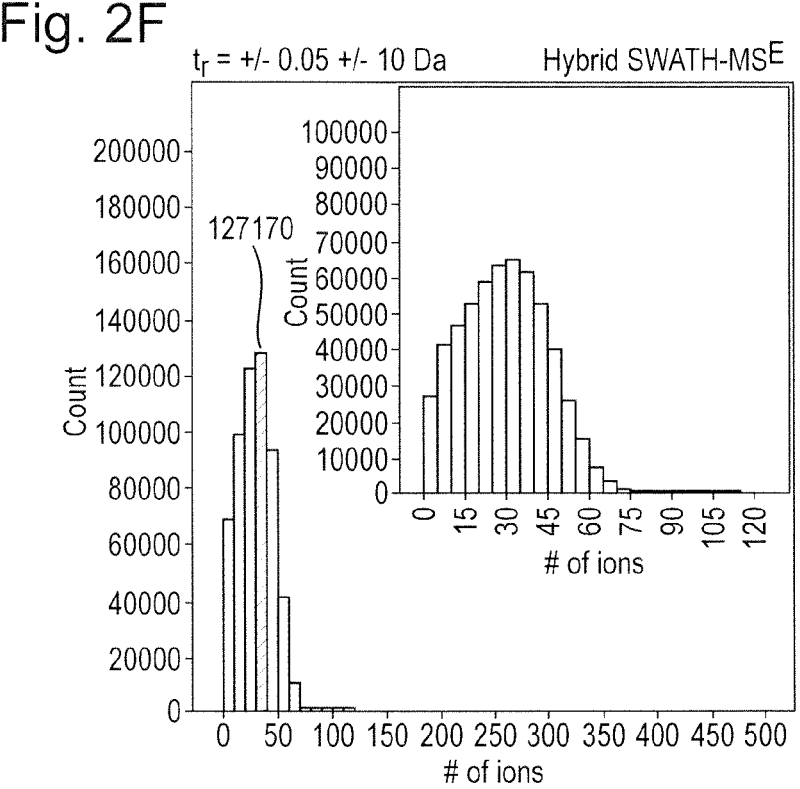
FIG. 2F shows the ion density distribution from a hybrid SWATH-MS$^E$ acquisition according to an embodiment wherein the chromatographic retention time $t_r$=±0.05 and a ±10 Da mass isolation window was used.
Figure 2G:
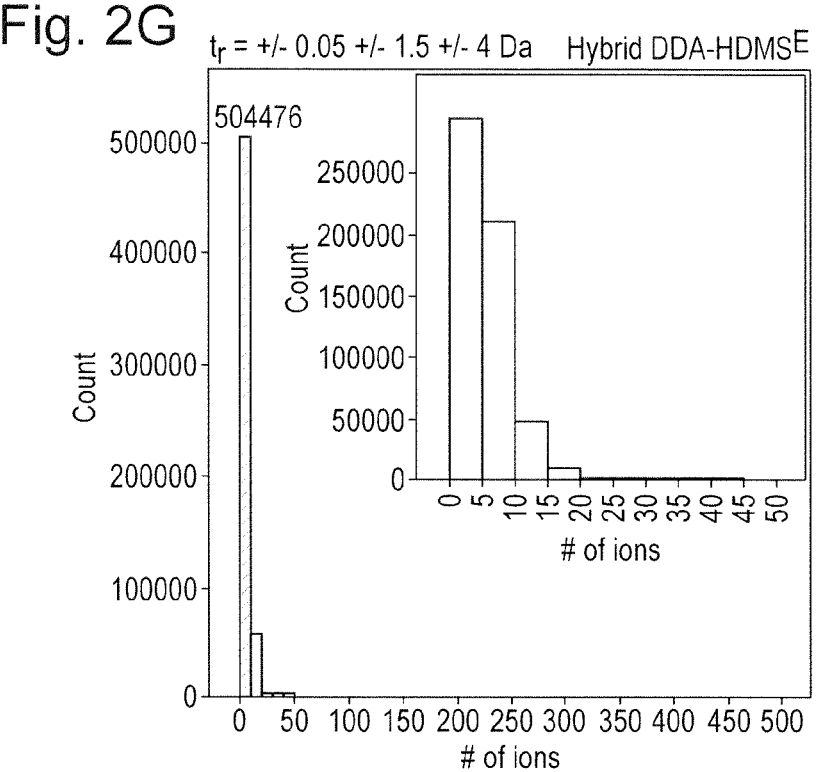
FIG. 2G shows the ion density distribution from a hybrid DDA-HD-MS$^E$ acquisition according to an embodiment wherein the chromatographic retention time $t_r$=±0.05, the ion mobility drift time was ±1.5 and a ±4 Da mass isolation window was used
Figure 2H:
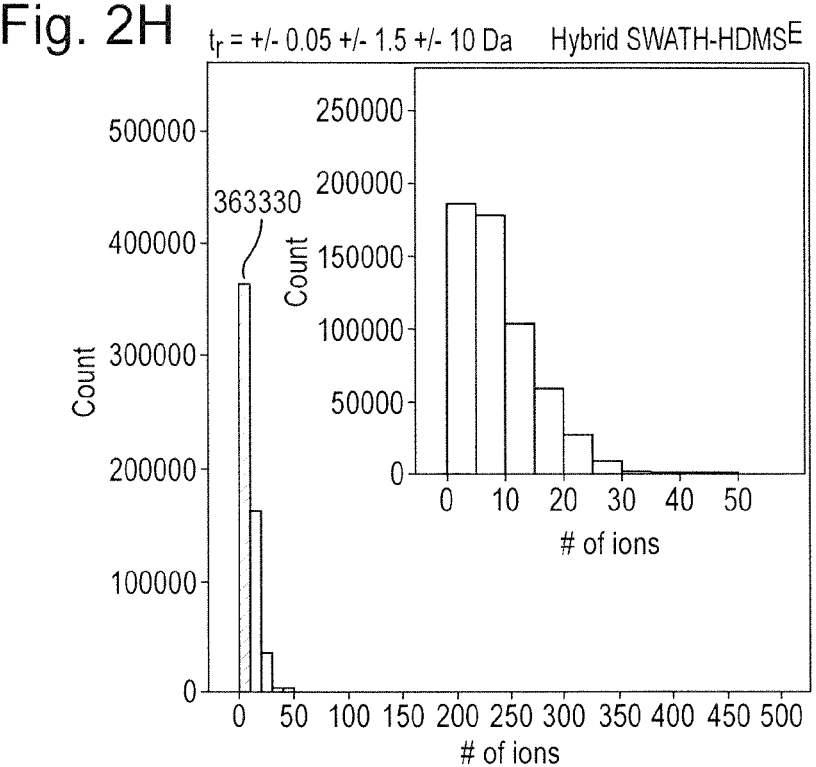
FIG. 2H shows the ion density distribution from a hybrid SWATH-HD-MS$^E$ acquisition according to an embodiment wherein the chromatographic retention time $t_r$=±0.05, the ion mobility drift time was ±1.5 and a ±10 Da mass isolation window was used.

FIGS. 2C and 2D illustrate the ion density distribution results from two conventional Data Independent Acquisitions strategies namely $MS^E$ and HD-$MS^E$ respectively.

FIG. 2C illustrates the compromise of increased chimeracy resulting from a $MS^E$ experiment. Though compromised in chimeracy, the $MS^E$ acquisition strategy has no sensitivity issues. It will be understood that the Data Dependent Acquisition method is limited in sensitivity whereas the Data Independent Acquisition $MS^E$ strategy is limited by chimeracy.

FIG. 2D shows the ion density distribution of a conventional Data Independent Acquisition HD-$MS^E$ acquisition. It is apparent that the ion density distribution is of similar width and position as the wider mass isolation window SWATH-Data Dependent Acquisition method as shown in FIG. 2B but without any negative effects on sensitivity. The selectivity of the method allows for a 20%-30% sampling of the entire ion flux.

An embodiment will now be described.

An embodiment is concerned with overcoming limitations associated with conventional methodologies and increasing the selectivity of workflows in order to enhance clarity and depth of coverage in complex systems samples.

FIGS. 2E-H illustrate the improvement in ion density distributions which may be obtained according to an embodiment. The distributions illustrate how a hybrid workflow which may be implemented according to an embodiment significantly increases the specificity of ion alignment with very little, if any, negative effects in terms of sensitivity.

The use of a highly efficient stacked ring ion guide to transmit ions has resulted in the fact that it has not been possible to optimally load the LC column without saturating the ion detector. Given the 10× increase in ion transmission afforded by high performance ion optics then high quality mass spectral data can be acquired at ~1/10$^{th}$ the on-column load.

The significant increase in ion transfer provides the means to increase the selectivity of the workflow by enabling the acquisition of data at higher mass resolving powers with no concurrent decrease in sensitivity by optimally loading the column.

Accepting that ion detector saturation is a function of ion strikes per unit time, increasing the on-column load back to its' optimal without a concurrent increase in mass resolution will exacerbate the distortion at higher loadings. However, mass analysers measure charged ions (isotopes) of eluting compounds, the number and distribution of which is directly proportional to the compounds' elemental composition and concentration. As such, by definition, any eluting compound whose most abundant isotopes are in saturation must have others that are not. With this being the case and given the fact that isotopic distributions can be calculated, the presence of a few correctly characterised isotopes to a molecular entity allows for determining the correct area of those in saturation thus increasing the linearity at the higher end of the experimental dynamic range. The lower end of the dynamic range is fixed i.e. the Limit of Detection ("LOD") of the instrument is fixed, whereas the upper end can be extended by sliding the linear portion of the signal versus loading plot across the section of the isotopic cluster that is not in saturation. Optimal loading of the column under these conditions will significantly improve the sensitivity of Data Dependent Acquisition experiments. Given that fragment or product ions are substantially lower in intensity than their corresponding parent or precursor ions, the saturation effect even on highly abundant parent or precursor ions will be negligible.

To increase both clarity and depth of coverage in complex systems requires firstly, maximizing both the sensitivity and dynamic range of the employed workflow. Secondly, enhanced selectivity (peak capacity) requires the ability to measure the physico-chemical attributes of each ion independent of all others. Thirdly, it is necessary to accurately align parent or precursor ions with their corresponding fragment or product ions and only their fragment or product ions. This enhancement in ion alignment is key and affords the opportunity to query exceedingly large search spaces for all types of chemical and post-translational modifications as well as point mutants and truncations with an exceedingly high degree of specificity. This ensures that the mass spectral data provides substantially improved qualitative and quantitative results.

FIG. 3 illustrates how the time potentially available during the elution of an ion peak is utilised intelligently according to an embodiment in order to maximize the selectivity. As described above a typical chromatographic peak width, as illustrated for example in FIG. 1H, may be approximately 15 s at half height. 15 s utilizing 120 ms acquisitions (150 ms including inter-scan delays) would enable 100 acquisitions to be performed across the ion peak.

However, it is not necessary to perform 100 scans in order to characterize the physico-chemical attributes of an ion peak. If it is assumed that 10 scans for accurate quantification across both the low and elevated energy peaks in a $MS^E$ or $HD\text{-}MS^E$ experiment will be sufficient then the time equivalent to 80 scans can potentially be freed up for other uses. According to an embodiment low energy, high energy and DDA acquisitions can be performed during the same cycle (which may last approximately 1.5 s) so that 10 cycles could be performed during the elution of a 15 s ion peak.

Conventional acquisition software provides for precursor ion discovery ("PID") acquisitions.

According to an embodiment a multifunction acquisition may be performed including both low and elevated energy channels (channels #1 and #2) and up to six Data Dependent Acquisitions (channels #3-8) as well as a centroided lock mass (channel #9). Nine functions each acquiring a data point every 150 ms leaves 150 ms for any additional time required for inter-scan delays. Keeping in mind the increase in ion transfer afforded by the stack ring ion guide and the 120 ms MS/MS acquisition time, the negative effect of partial peak sampling due to the Data Dependent Acquisition is effectively minimized.

Figure 4A:
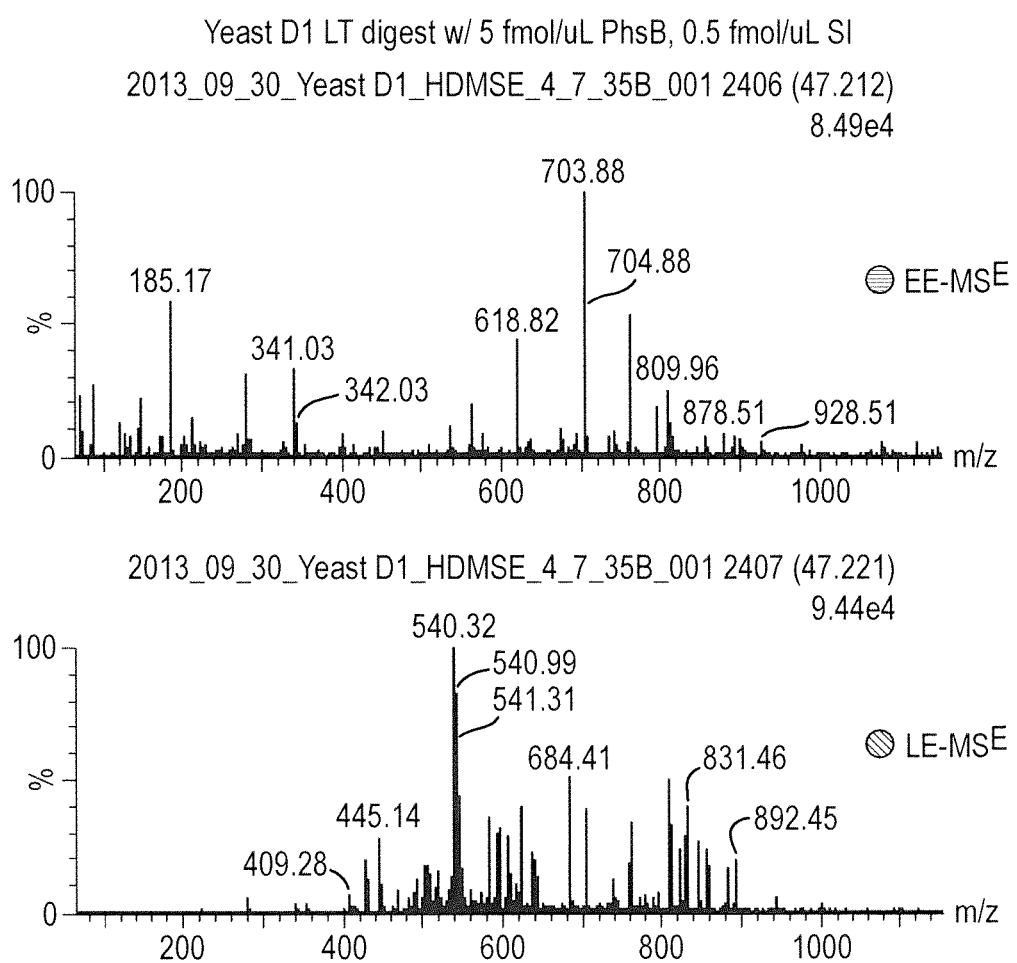
FIG. 4A illustrates an embodiment wherein one low energy acquisition (LE-MS$^E$) and one high energy or elevated energy acquisition (HE-MS$^E$) are performed at the start of each cycle.
Figure 5:
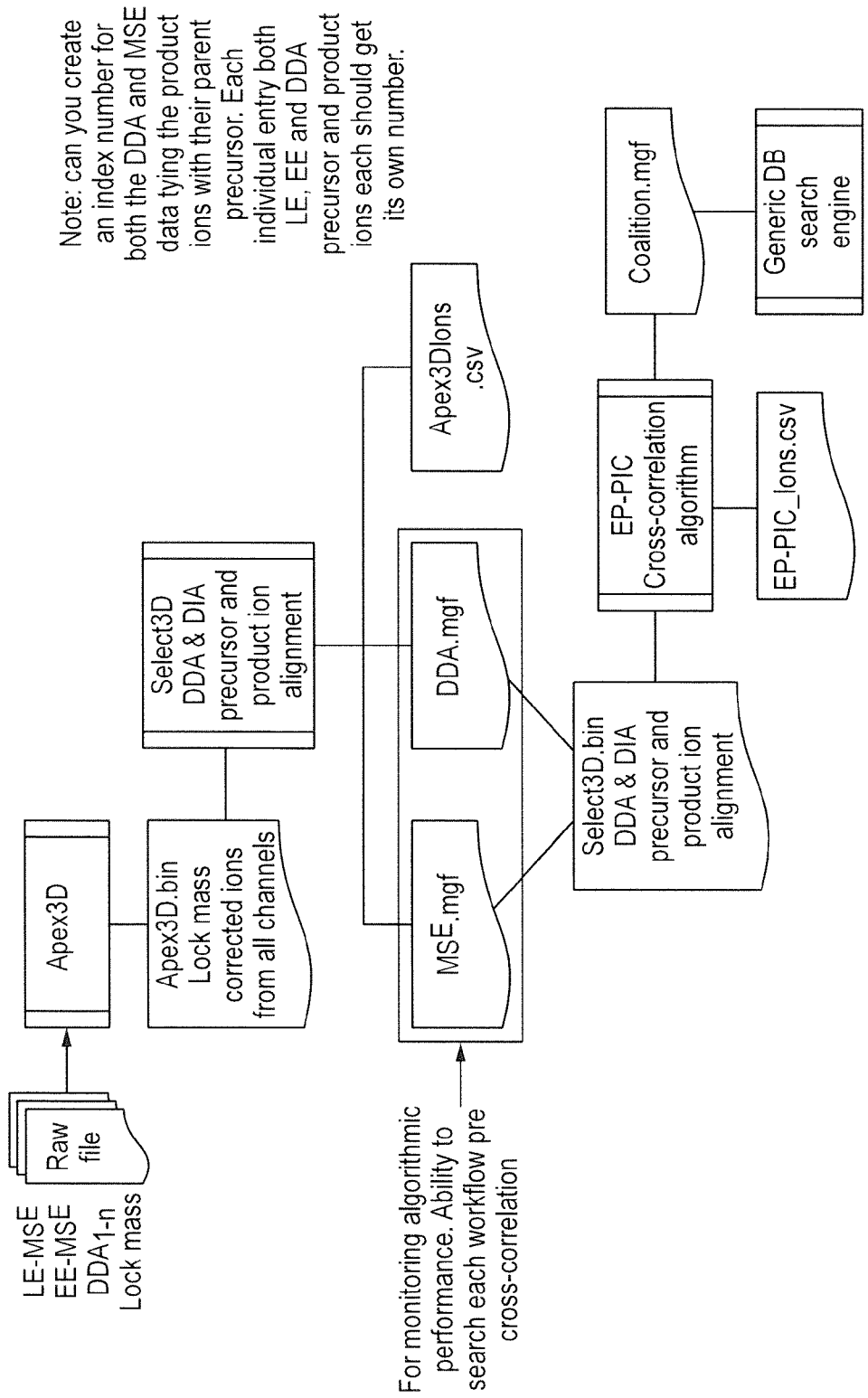
FIG. 5 shows an example workflow.

FIGS. 4A-AC illustrate an example cycle of operation lasting 1.5 s which may comprise initially performing a low energy $MS^E$ acquisition followed by a high energy $MS^E$ acquisition. Thereafter, six DDA MS/MS acquisitions may be performed. Eight cycles, each lasting 1.5 s, may for example be performed across each chromatographic peak as measured at FWHM as shown in FIG. 4B FIG. 5 shows an example workflow which will be discussed in more detail below.

DDA Processing

A DDA ion detection algorithm can be utilised which may serially process each DDA channel extracting the mass to charge ratio, retention time and/or retention time and ion mobility drift time of each switched ON precursor ion. The algorithm may then align each parent or precursor ions with their respective mass resolved product or fragment ions.

Once precursor-product ion lists have been generated then each switched ON precursor ion may be queried against the low-energy $MS^E$ or $HD\text{-}MS^E$ charge clusters to ensure that the switched ON mass to charge ratio is indeed the $A_0$ molecular ion and to identify all $A_0$ ions from any and all other co-eluting and co-fragmenting ion clusters within the DDA experimental precursor ion isolation window. In instances where there exists additional precursor ions within the isolation window, the product ions aligned to the fiducial precursor are also assigned to each of the "virtual" precursor ion clusters found to be present within the DDA experimental mass selection window. The copied product ions are restricted to only those with a mass less than the monoisotopic mass of the precursor and within a user defined or algorithmically derived intensity ratio. Algorithmically, the program finds the residual precursor charge cluster or charge reduced charge cluster and subtracts the summed area of it from the summed area of the parent cluster allowing only product ions whose area is within the subtracted area and either a user defined or algorithmically determined intensity ratio. The ability to find the residual ion cluster in either the DDA MS/MS or elevated-energy spectrum is a function of the applied collision energy or collision energy ramp, DDA and $MS^E$ or $HDMS^E$ respectively, as well as the bond energies of the precursor ions undergoing disassociation. It is generally accepted that the proper collision energy or collision energy ramp for precursor ion dissociation results in a residual ion cluster area of ~30% that of the parent. A higher percent and the ion is considered under fragmented, a lower and the ion is considered over fragmented.

Given that a precursor ion, when dissociated, produces many shorter multiples of itself, each occupying a mass-sufficient mass to charge ratio space, chimeracy can become a severely limiting factor. How much chimeracy a workflow can handle is primarily dependent on how many product ions are generated and how well their physicochemical attributes can be measured. The ultimate goal of an embodiment is to produce very clean high mass accuracy MS/MS and elevated energy spectra. To that end, an embodiment applies a collision energy or collision energy ramp lower then what has been previously practiced. A residual summed ion area of about 40-50% may be used. Unlike lower resolution MS/MS spectra where it is the linear sequence of amino acids that provides the specificity for accurate identifications, the increased mass accuracy of product ions in conjunction with site specificity of the weaker bond energies, retention time and/or cross sectional area or drift time prediction models provides the means to make very accurate identifications from very few product ions. Here the principal factor for accurate identification is the specificity of alignment, simply the aligned product ions are exclusive to the parent precursor. This is why embodiments can be so successful in querying very large search spaces with high accuracy. In addition, less product ions allow for wider isolation windows. Wider isolation windows allows for greater numbers of mass resolved precursor-product ion lists that can be compared to their time and/or time and drift resolved companions, thus increasing both the selectivity and specificity of embodiments.

In a DDA workflow the switch in intensity is generally set to the apex intensity of the least abundant ion of interest. With this being the case rarely if ever will a precursor ion be switched ON at its chromatographic apex as such a match tolerance in chromatographic retention time between the switched ON time in the DDA portion of the hybrid workflow and the center mass retention time in the $MS^E$ or $HD\text{-}MS^E$ portion may vary by as much as +/− an entire chromatographic peak width (FWHM). When verifying that the switched ON mass is the $A_0$ molecular ion and identifying the co-fragmenting ion clusters present in the ion transmission the algorithm cannot use the reported center mass retention time for the reasons previously described. The low energy ion detection algorithm in addition to calculating the FWHMs in each of the three dimensions of mass to charge ratio, chromatographic retention time and ion mobility drift also reports the takeoff, landing and up and down slope inflexion points in both chromatographic retention time and/or chromatographic retention time and ion mobility drift time. With this being the case the matching (switched ON to low energy) algorithm queries the interval between takeoffs and landings for the co-eluting ion clusters. Given the increased retention-time match tolerance necessitated by the DDA ion selection process the matching part of the algorithm relies more on the higher mass accuracy afforded by the increased mass resolving power (and when utilised ion mobility drift time) to correctly select the companion low-energy precursor. In instances where there is more than one low energy ion in the precursor ion selection window the aligned product ions are compared and the one with the highest number of matched product ions is selected as the companion. Once the appropriate low-energy ion cluster is identified the integrity of the switch ON ions' status as an $A_0$ molecular ion can be validated or adjusted.

Once the co-eluting, co-fragmenting precursor ion clusters have been identified in the low-energy $MS^E$ and/or HDMS$^E$ processed data, the algorithm creates a "virtual" MS/MS spectrum for each one. For each "virtual" precursor, the physicochemical attributes (e.g. mass to charge ratio, chromatographic retention time and ion mobility drift time) emanate from the MS$^E$ and/or HDMS$^E$ processed copied from the references' DDA spectrum. The inclusion of ion mobility drift time as a physicochemical attribute of the "virtual" precursor significantly enhances the algorithm's ability to correctly parse the matched (mass resolved DDA product ions to the chromatographic retention time and/or chromatographic retention time and ion mobility drift resolved MS$^E$ or HD-MS$^E$ product ions) product ions across each of the "virtual" precursors. These "virtual" product ion spectra are then filtered by mass and intensity. With respect to mass, the assigned fragment ions must be less than the mono-isotopic mass of their parent precursor. As for the area restriction, as before, the algorithm will first look for the residual ion cluster of the parent in the MS/MS spectrum. If found, the area of the residual ion cluster is subtracted from that of the parent and the assigned product ion areas are restricted to a maximum of 1.5× the subtracted area to a minimum of the subtracted area divided by either a user defined or algorithmically set value. Again, given the serial nature of DDA acquisitions, the time a precursor ion is selected to when it is fragmented varies with the acquisition time and its place in the switch list as such it is possible to produce a product ion of higher intensity than its parent precursor.

The DDA processing terminates with mass and area restricted product ion spectra for all switched ON and "virtual" precursor ions, each with a validated $A_0$.

MS$^E$ and HD-MS$^E$ Processing

The data relating to the "Global" portion of the hybrid workflow resides in channels #1 and #2. This data is very similar to that of a conventional MS$^E$ or HD-MS$^E$ acquisition with the only difference being the frequency of acquisition.

FIGS. 4A-4C depicts the cycling of acquisition according to the hybrid workflow according to an embodiment. Channels #1 and #2 are processed with a variant of the ion detection algorithm that reports the physicochemical attributes of each low and elevated energy ion at its' chromatographic retention time, mass to charge ratio and if implemented ion mobility drift time apex. In addition, each attribute is further annotated with its' takeoff, landing and upslope and downslope inflexion points. The takeoff and landing points are useful if identifying the "virtual" precursors present in the ion selection window of the DDA portion of the workflow.

To begin, a user may set a minimum area threshold for the low and elevated energy ion detections to be considered for clustering in to precursor ion charge groups. In addition, the user may input the minimum summed area of all the isotopes participating in the charge group. De-isotoping into charge groups may be performed by a second algorithm ("Select3D"). The de-isotoping algorithm may limit both the low and elevated-energy ion detections to either a user defined or algorithmically determined maximum.

Once the ion lists have been attuned the low-energy ions may be sorted from lowest mass to charge ratio to highest mass to charge ratio. Starting at the maximum allowable charge state z (function of the mass resolving power of the experiment as calculated by the ion detection algorithm) a Δ mass as defined by 1.007/z is added to the selected low-energy ion and the resulting mass is queried against the remaining low-energy ions employing again either a series of user or algorithmically defined match factors. A match factor is either a fraction or integer value applied to the attributes' calculated FWHM. This process creates a three-dimensional window for gathering isotopes for the creation of charge groups.

Ions passing the match criteria may then be grouped into a candidate isotopic cluster. At this point the algorithm may use the mass to charge ratio of the $A_0$ molecular ion to generate a theoretical isotope model of the charge cluster. The algorithm may compare the isotopic distributions of the model to that of the candidate cluster. Any isotope of the candidate cluster can have an intensity greater than the predicted value due to un-resolved overlapping ion(s). In this instance, the algorithm may allow for a calculated variance in intensity, remove the excess, leaving the residual for subsequent assignment.

Once the precursor charge cluster has been created and validated, the algorithm may then query the chromatographic retention time and/or chromatographic retention time and ion mobility drift aligned product ions to search for the residual (un-fragmented) fiducial (most intense isotope) ion in the elevated energy mass spectral data. The de-isotoping algorithm may utilize the match factors in a fashion similar to that previously described above. Once the fiducial ion has been located in the elevated energy mass spectral data, the de-isotoping algorithm may then be used to construct and validate the residual charge cluster.

Given, the cycling of the hybrid acquisition strategy as illustrated in FIGS. 4A-4C, there is a likelihood for variance in cadence between the two acquisition methods. According to an embodiment the residual charge cluster may be used to provide two important enhancements to product ion alignment. Firstly, the residual ion cluster establishes the three dimensional positioning in chromatographic retention time, ion mobility drift time and mass to charge ratio of the associated product ions given that product ion by definition must follow the same chromatographic retention time and ion mobility drift time profiles as their residual ion cluster. This process corrects for any movement in mass to charge ratio, chromatographic retention time and/or ion mobility drift time of the product ions caused by either the inlet and/or the mass analyser as well as the employed hybrid workflow. Secondly, the summed area of the residual ion cluster is subtracted from that of its parent precursor resulting in a metric for determining the minimum and maximum area of the chromatographic retention time and/or chromatographic retention time and ion mobility drift aligned product ions. The rationale for filtering of product ions by area counts is evident by the fact that a precursor ion cluster cannot produce a product ion of greater intensity then that of the calculated difference between the precursor ion and residual summed ion cluster areas. As for the minimum allowable product ion area the calculated fragmentation efficiency may be utilised which is determined by the expression: 1−summed residual ion cluster area divided by that of its parent precursor to set the minimum.

Completion of both the DDA and MS$^E$ (or HD-MS$^E$) processing culminates in two comprehensive lists of precursor-product ion tables that may be used as an input to an "Amalgorithm" routine.

Amalgorithmic Processing

In order to enhance clarity and depth-of-coverage in the analysis of complex biological "system" requires highly selective precursor and product ion alignment. In this context clarity can be achieved by combining or uniting the mass resolved DDA and chromatographic retention time and/or chromatographic retention time and ion mobility drift resolved MS$^E$ or HD-MS$^E$ product ion spectra resulting in a composite "cleaned" product ion spectrum consisting primarily of product ions unique to each parent. In an embodiment the algorithmic process referred to an "amalgamation" for generating these "cleaned" product ion spectra begins by firstly calculating the median chromatographic retention time, mass to charge ratio and ion mobility drift time FWHM of the low-energy ion detections present in the $MS^E$ or HD-$MS^E$ data.

The inputted composite DDA precursor-product ion table may then be sorted in descending order of precursor ion intensity and the fiducial ion of the most abundant DDA precursor may be selected for querying the precursor ion clusters from the composite precursor-product ion table of the companion $MS^E$ or HD-$MS^E$ dataset. The fiducial ions' may be paired in a fashion similar to that previously described for forming charge clusters.

Again, as previously described in the DDA processing section, the preset switch in intensity in a DDA experiment is typically set to the apex intensity of the least abundant ion of interest. As such, rarely if ever, will a precursor ion be switched on at its chromatographic retention time apex. With this being the case, the match factor for determining the chromatographic retention time window for matching, may be set to 2× the median chromatographic retention time FWHM. Since mass accuracy is not a function of ion type, the match factor in mass may be set similar to all other mass match processes. In the DDA acquisition, ion mobility separation may be applied after the collision induced dissociation ("CID") stage so that ion mobility drift time at this time is not utilized for selecting the companion fiducial ion from the HD-$MS^E$ data albeit once the product ions have been matched and validated the ion mobility drift time may be utilized for enhancing product ion alignment in all associated "virtual" DDA product ion spectra.

The algorithm may set the match windows in chromatographic retention time and mass to charge ratio and the selected precursor product ion tables from the $MS^E$ or HD-$MS^E$ are extracted in descending order of precursor ion intensity for further consideration. At this time the algorithm may compare both the calculated mono-isotopic mass of the precursor and the Δ area (precursor-residual) to a model predicting the minimum number of product ions to match given the inputted mass to charge ratio and Δ area before performing spectral cleaning. If the wrong precursor product ion table is paired then the match ratio (matched/predicted) drops below 1 and both clusters tables are left intact and a second attempt may be made at matching the correct companion. The algorithm may repeat until all the possible matched pairs are exhausted.

In instances when the match has been validated, match ratio >1, the matched mass to charge ratio values are averaged, the ion areas summed and the drift time from the HD-$MS^E$ is added. Given that each ion detection in both the DDA and $MS^E$ or HD-$MS^E$ processing is assigned a unique index number once matched and validated all $MS^E$ or HD-$MS^E$ matched ions including their isotopes are depleted from all remaining $MS^E$ or HD-$MS^E$ precursor and product ion tables. Conclusion of the "amalgorithmic" process may result in cleaned filtered precursor product ion tables that can then be queried against very large search spaces for any and all types of chemical, post-translational modifications, point mutations and single nucleotide polymorphisms to name only a few. Though the size of the database will be very large, the specificity of the product ion alignment in conjunction with the high mass accuracy of both precursor and product ions in addition to, the orthogonality of employed analytical workflow comprising higher mass resolution, ultra high pressure liquid chromatography separations and ion mobility separations in conjunction with the example hybrid workflow may effectively guarantee that only the correct parent molecule is identified.

With respect to quantification given the de-isotoping algorithms employment of strict isotope modelling, cluster comparison and validation models ensure that the areas assigned to each parent precursor ion cluster emanate from their parent eluting compound and only their parent eluting compound.

Example Embodiment

FIGS. 6A-B illustrate in more detail an example embodiment. FIG. 6A shows base peak intensity ("BPI") chromatograms of the low and elevated-energy Data Independent Acquisitions channels and FIG. 6B shows total ion currents for the six Data Dependent Acquisition channels (channels #3-8). Channel #9, namely the lock mass channel, is not shown.

It will be understood that any fragment or product ion detected in a Data Dependent Acquisition spectrum must also be present in a corresponding Data Independent Acquisition although in the Data Dependent Acquisition channel fragment or product ions are formed from parent or precursor ions that are mass resolved (quadrupole isolation window) whereas in the Data Independent Acquisition channels fragment or product ions are formed from parent or precursor ions that are time resolved ($MS^E$) and/or time resolved and ion mobility drift time (HD-$MS^E$) resolved.

This difference in how the parent or precursor ions are resolved prior to Collision Induced Dissociation fragmentation provides the necessary orthogonality to align parent or precursor ions and corresponding fragment or product ions with the exceedingly high selectivity necessary to query a very large search space with high selectivity. Fragment or product ions may only be assigned to parent or precursor ions within the mass isolation window exhibiting the same center mass retention time (and if ion mobility separation is employed center mass retention time and ion mobility drift time) within the user defined match tolerances.

In instances where there is more than one parent or precursor ion sharing very similar attributes in terms of mass to charge ratio, chromatographic retention time and ion mobility drift time then a plurality of fragment or product ions will be assigned to each parent or precursor ion. The selectivity of alignment can be further improved by utilising a RDIF ("Relative mass Defect Ion Filter"). Only ions that match are retained in the Data Dependent Acquisition spectrum list.

The intensities associated with the matched fragment or product ions is the sum of both acquisition methods.

In known third party search engines the relative intensity of the fragment or product ions that match relative to those that do not is a relatively large part of the scoring algorithm. Reducing the fragment or product ions to only those that conform and summing the intensities significantly affects the depth-of-coverage due to the high specificity and ion counts regardless of which search engine is employed.

An embodiment is therefore concerned with the intersection of mass resolved product ion data with retention time and/or retention time and ion mobility drift time resolved data of the same parent or precursor ion in the same experiment or across experiments.

Current state of the art with respect to MS or MS/MS acquisition methods are Data Dependent Acquisitions and Data Independent Acquisitions. Conventionally, the two different methods are run independently.

An embodiment relates to a workflow that combines the two different acquisition methods into a single experimental workflow.

Sensitivity is a function of ion flux. The narrower a chromatographic peak the higher the ion flux. Higher ion flux allows for faster acquisition times.

A current state of the art liquid chromatography system comprising an optimally loaded column running a 90 minute gradient separation will generally produce chromatographic peak widths of ~10-15 s at half-height. The ion transfer efficiency of current state of the art ion sources in addition to the speed of the acquisition electronics enables scan speeds of 80-100 ms to be readily achieved.

Given a typical peak width of 10-15 s then the mass analyser can acquire between 100-150 scans (including inter-scan delay times) across each chromatographic peak.

It will be understood by those skilled in the art that correct quantitative measurements can be achieved with, for example, only 7-10 scans across a typical Gaussian peak. With this being the case, it is possible to be more efficient in how time is used.

Using time more efficiently enables a low-energy $MS^E$ or HD-$MS^E$ parent ion scan followed by an elevated-energy $MS^E$ or HD-$MS^E$ fragment or product ion scan to be followed by a plurality of Data Dependent Acquisitions to be performed during a single cycle according to an embodiment.

Given the sensitivity limitations of Data Dependent Acquisitions (due to partial peak sampling and isolation widths) the scan speed is limited to 80-100 ms albeit because of the additional orthogonality of the $MS^E$ or HD-$MS^E$ functions the size of the isolation width may be increased to catch more parent or precursor ions as well as increasing the sensitivity of each Data Dependent Acquisition.

How wide to make the isolation window will be a function of sample complexity and specificity (mass resolution, ion mobility separation, peak width) of the employed instrumentation.

Parent or precursor ion selection may be accomplished by intensity at the time of the MS survey scan or by a targeted include/exclude list. In either case the maximum number of MS/MS functions will be dictated by scan speed and chromatographic peak width.

The two Data Independent Acquisitions may be processed utilizing a modified ion detection method. Parent or precursor ions may be clustered by charge-group and fragment or product ions may be assigned by matching center mass retention-time and/or center mass retention and ion mobility drift times within a specified tolerance(s).

Data Dependent Acquisition data may be processed in a similar fashion albeit each selected mass to charge ratio may be located in the processed low-energy $MS^E$ or HD-$MS^E$ survey scan or parent ion data whereby the isolation window is applied and the mass resolved product ions may be assigned to each co-fragmenting parent or precursor ions in a one-to-many relationship creating new virtual MS/MS spectra.

Some filtering of the product ions may be performed during this re-binning process. Product ions cannot be greater in mass than their parent and their intensity may be limited by applying an intensity prediction filter.

Given that both data types have been processed prior to the creation of the virtual Data Dependent Acquisition spectra, the center mass retention and/or center mass retention and ion mobility drift times may be recorded for each newly created Data Dependent Acquisition parent or precursor ion.

After both data types have been processed, the MS/MS spectra may be sorted in decreasing parent or precursor ion intensity. Starting with the most abundant switched ON mass to charge ratio, the method may locate its corresponding Data Independent Acquisition time and/or time and ion mobility drift time aligned companion. Applying a mass to charge ratio match tolerance, a fragment ion count model (an estimate of the minimum number of product ions that should be matched to a parent or precursor ion of a given mass to charge ratio and intensity) and an intensity model (the Data Independent Acquisition matched ion intensity has to be greater than the Data Dependent Acquisition) restricts the MS/MS spectra to only the intersecting ions.

If the predicted minimum is not breached then the spectrum is left intact and the enhanced alignment method may move to the next parent or precursor ion in the list. Next, the intensities of the matched pairs are summed and the matched Data Independent Acquisition ions are removed from the entire Data Independent Acquisition dataset. Similarly, the matched product ions from the Data Dependent Acquisition spectrum are removed from the co-fragmenting parent or precursor ions provided their center mass retention and/or center mass retention and ion mobility drift time is not within the match tolerance of selected parent or precursor ions. Under these conditions the product ions cannot be further reduced due to the fact that their parent or precursor ions are all located within the mass, time and ion mobility drift alignment windows.

Recalling that the main compromise associated to Data Independent Acquisition analyses is chimeracy, product ions can be distributed across many parent or precursor ions. The depletion loop removes the matched ions from all Data Independent Acquisition parent or precursor/product ion lists.

The described process may be repeated until each collected and virtual Data Dependent Acquisition spectrum has been cleaned by its Data Independent Acquisition counterpart as well as each remaining Data Independent Acquisition spectrum has been cleaned by its companion Data Dependent Acquisition. Application of the hybrid workflow and the post-processing re-alignment and depletion methods according to an embodiment result in a more comprehensive cleaned list of parent or precursor ions and product ions than any other platform is currently able to provide.

Although the present invention has been described with reference to various embodiments, it will be understood by those skilled in the art that various changes in form and detail may be made without departing from the scope of the invention as set forth in the accompanying claims.

The invention claimed is:

1. A method of mass spectrometry comprising:
    using an ion source to ionise a sample eluting from a separation device that is upstream of said ion source in order to generate a plurality of parent ions, wherein said separation device comprises at least one of: a liquid chromatography separation device; a gas chromatography separation device; a capillary electrophoresis separation device; a capillary electrochromatography separation device; a substantially rigid ceramic-based multilayer microfluidic substrate separation device; or a supercritical fluid chromatography separation device; and
    performing multiple cycles of operation as said sample elutes from said separation device, wherein each cycle of operation comprises the steps of:
    (i) mass analysing said parent ions to obtain parent ion mass spectral data;

(ii) transmitting said parent ions to a fragmentation or reaction device without substantially mass filtering said parent ions, causing said parent ions that have not been substantially mass filtered to fragment or react to form fragment or product ions and obtaining fragment or product ion mass spectral data;

(iii) mass filtering said parent ions so that first parent ions having mass to charge ratios within a first mass to charge ratio range are onwardly transmitted to a fragmentation or reaction device, causing said first parent ions to fragment or react to form first fragment or product ions and obtaining first fragment or product ion mass spectral data; and (iv) mass filtering said parent ions so that second parent ions having mass to charge ratios within a second different mass to charge ratio range are onwardly transmitted to a fragmentation or reaction device, causing said second parent ions to fragment or react to form second fragment or product ions and obtaining second fragment or product ion mass spectral data.

2. A method as claimed in claim 1, wherein each cycle of operation further comprises the step of:

(v) mass filtering said parent ions so that third parent ions having mass to charge ratios within a third different mass to charge ratio range are onwardly transmitted to a fragmentation or reaction device, causing said third parent ions to fragment or react to form third fragment or product ions and obtaining third fragment or product ion mass spectral data.

3. A method as claimed in claim 2, wherein each cycle of operation further comprises the step of:

(vi) mass filtering said parent ions so that fourth parent ions having mass to charge ratios within a fourth different mass to charge ratio range are onwardly transmitted to a fragmentation or reaction device, causing said fourth parent ions to fragment or react to form fourth fragment or product ions and obtaining fourth fragment or product ion mass spectral data.

4. A method as claimed in claim 3, wherein each cycle of operation further comprises the step of:

(vii) mass filtering said parent ions so that fifth parent ions having mass to charge ratios within a fifth different mass to charge ratio range are onwardly transmitted to a fragmentation or reaction device, causing said fifth parent ions to fragment or react to form fifth fragment or product ions and obtaining fifth fragment or product ion mass spectral data.

5. A method as claimed in claim 4, wherein each cycle of operation further comprises the step of:

(viii) mass filtering said parent ions so that sixth parent ions having mass to charge ratios within a sixth different mass to charge ratio range are onwardly transmitted to a fragmentation or reaction device, causing said sixth parent ions to fragment or react to form sixth fragment or product ions and obtaining sixth fragment or product ion mass spectral data.

6. A method as claimed in claim 1, wherein each cycle of operation further comprises the step of:

supplying or mass analysing lockmass or calibration ions in order to check or adjust a mass to charge ratio calibration of a mass spectrometer.

7. A method as claimed in claim 1, wherein steps (i) and (ii) comprise a Data Independent Acquisition mode of operation.

8. A method as claimed in claim 1, wherein steps (iii)-(iv) comprise a Data Dependent Acquisition mode of operation.

9. A method as claimed in claim 1, further comprising determining the mass to charge ratios of parent ions from said parent ion mass spectral data.

10. A method as claimed in claim 1, wherein the step of mass filtering said parent ions comprises setting the mass to charge ratio transmission window of a mass filter so as to onwardly transmit parent ions having a mass to charge ratio which corresponds with a mass to charge ratio of parent ions determined to be present in said parent ion mass spectral data.

11. A method as claimed in claim 10, wherein the step of mass filtering said parent ions comprises setting the mass to charge ratio transmission window of a mass filter so as to attenuate other ions which do not correspond with said parent ions determined to be present in said parent ion mass spectral data.

12. A method as claimed in claim 1, wherein the duration of each cycle of operation is selected from the group consisting of: (i) <0.5 s; (ii) 0.5-1 s; (iii) 1-1.5 s; (iv) 1.5-2 s; (v) 2-2.5 s; (vi) 2.5-3 s; and (vii) >3 s.

13. A method as claimed in claim 1, wherein during step (i) parent ions are not substantially subjected to fragmentation or reaction.

14. A method as claimed in claim 1, wherein step (i) is performed prior to or subsequent to step (ii) during at least some or substantially all cycles of operation.

15. A method as claimed in claim 1, wherein at least on of step (i) and step (ii) is performed prior to or subsequent to at least on of step (iii) and step (iv) during at least some or substantially all cycles of operation.

16. A method as claimed in claim 1, wherein the intensity of fragment or product ions having a particular mass to charge ratio is determined from summing the intensity of said fragment or product ions from at least one of said fragment or product ion mass spectral data, said first fragment or product ion mass spectral data and said second fragment or product ion mass spectral data.

17. A method as claimed in claim 1, wherein at least one of step (i), step (ii), step (iii) and step (iv) further comprises separating and/or selecting parent ions and/or fragment or product ions according to their ion mobility or differential ion mobility.

18. A method as claimed in claim 1, wherein said sample comprises a biological, organic, inorganic, chemical or pharmaceutical sample.

19. A method as claimed in claim 1, wherein said sample comprises a complex mixture of biomolecules or organic molecules.

* * * * *